US011834671B2

(12) United States Patent
Tanaka et al.

(10) Patent No.: US 11,834,671 B2
(45) Date of Patent: Dec. 5, 2023

(54) METHOD OF PRODUCING CANCER STEM CELLS

(71) Applicant: National University Corporation Hokkaido University, Hokkaido (JP)

(72) Inventors: Shinya Tanaka, Hokkaido (JP); Kazunori Yasuda, Hokkaido (JP); Jian Ping Gong, Hokkaido (JP); Masumi Tsuda, Hokkaido (JP); Takayuki Kurokawa, Hokkaido (JP)

(73) Assignee: National University Corporation Hokkaido University

( * ) Notice: Subject to any disclaimer, the term of this patent is extended or adjusted under 35 U.S.C. 154(b) by 1031 days.

(21) Appl. No.: 16/487,247

(22) PCT Filed: Feb. 20, 2018

(86) PCT No.: PCT/JP2018/005884
§ 371 (c)(1),
(2) Date: Dec. 6, 2019

(87) PCT Pub. No.: WO2018/151309
PCT Pub. Date: Aug. 23, 2018

(65) Prior Publication Data
US 2020/0095541 A1    Mar. 26, 2020

(30) Foreign Application Priority Data

Feb. 20, 2017    (JP) ................................. 2017-028833

(51) Int. Cl.
| | | |
|---|---|---|
| *C12N 5/00* | (2006.01) | |
| *C12N 5/095* | (2010.01) | |
| *G01N 33/50* | (2006.01) | |
| *C12Q 1/02* | (2006.01) | |

(52) U.S. Cl.
CPC ......... *C12N 5/0068* (2013.01); *C12N 5/0018* (2013.01); *C12N 5/0695* (2013.01); *C12Q 1/02* (2013.01); *G01N 33/5073* (2013.01); *C12N 2500/50* (2013.01); *C12N 2502/1352* (2013.01); *C12N 2533/30* (2013.01); *C12N 2535/00* (2013.01)

(58) Field of Classification Search
CPC .. C12N 5/0068; C12N 5/0018; C12N 5/0695; C12N 2533/30; C12N 2535/00; G01N 33/5073
See application file for complete search history.

(56) References Cited

U.S. PATENT DOCUMENTS

| 2005/0109976 A1* | 5/2005 | Fuchs | ..................... H01F 1/447 |
| | | | 252/62.53 |
| 2015/0175972 A1 | 6/2015 | Jabbari | |

FOREIGN PATENT DOCUMENTS

| JP | 2010158180 A | 7/2010 | | |
| JP | 2010174063 A | 8/2010 | | |
| JP | 2016083276 A | 5/2016 | | |
| JP | 2016523079 A | 8/2016 | | |
| KR | 20130138948 A | * 12/2013 | ............. | A61L 27/52 |
| WO | 2014/204406 A1 | 12/2014 | | |

OTHER PUBLICATIONS

Yin et al. Double network hydrogels from polyzwitterions: high mechanical strength and excellent anti-biofouling properties. Journal of Materials Chemistry B. p. 1-9 (Year: 2013).*
You et al. Matrix stiffness-mediated effects on stemness characteristics occurring in HCC cells. Oncotarget, vol. 7, No. 22, p. 32221-32231 (Year: 2016).*
You et al. Higher Matrix Stiffness Upregulates Osteopontin Expression in Hepatocellular Carcinoma Cells Mediated by Integrin β1/GSK3β/β-Catenin Signaling Pathway. PLOS ONE 10(8): e0134243, p. 1-13 (Year: 2015).*
Bhat, Krishna et al., "The transcriptional coactivator TAZ regulated mesenchymal differentiation in malignant glioma", Genes & Development, 25: 2594-2609 (2011).
Bora-Singh, Namrata et al., "YAP1 regulates OCT4 activity and SOX2 expression to facilitate self-renewal and vascular mimicry of stem-like cells", Stem Cells, 33(6): 1705-1718 (2015).

(Continued)

*Primary Examiner* — Taeyoon Kim
(74) *Attorney, Agent, or Firm* — Kathleen D. Rigaut; Howson & Howson LLP

(57) ABSTRACT

The present invention relates to a method of producing cancer stem cells that comprises culturing a living cell population containing cancer cells in the presence of a gel substance to obtain a living cell population containing cancer stem cells, wherein the gel substance is a material that induces expression of osteopontin in at least a portion of cells contained in the living cell population. Moreover, the present invention relates to an agent for inducing conversion of cancer cells to cancer stem cells that comprises a gel substance that induces expression of osteopontin in at least a portion of the cells contained in a living cell population. The gel substance is a synthetic polymer gel composed of, for example, double network gel, PNaSS gel, PCDME gel, PA gel, RAMPS gel, PDMA gel or PAAc gel. The present invention provides means and a method that enable the preparation of cancer stem cells in a relatively short period of time and at a relatively low culturing cost without requiring expensive equipment.

8 Claims, 24 Drawing Sheets

(56) References Cited

OTHER PUBLICATIONS

Cao, Lei et al., "Osteopontin promotes a cancer stem cell-like phenotype in hepatocellular carcinoma cells via an integrin-NF-B-HIF-1a pathway", Oncotarget, 6(9): 6627-6640 (2015).
Chen, Yong Mei et al., "Cultivation of endothelial cells on adhesive protein-free synthetic polymer gels", Biomaterials, 26: 4588-4596 (2005).
Chen, Yong Mei et al., "Platelet adhesion to human umbilical vein endothelial cells cultured on anionic hydrogel scaffolds", Biomaterials, 28: 1752-1760 (2007).
Dupont, Sirio et al., "Role of YAP/TAZ in mechanotransduction", Nature, 474: 179-183 (2011).
Gong, Jian Ping, "Materials both Tough and Soft", Science, 344: 161-162 (2014).
Goodell, Margaret et al., "Isolation and Functional Properties of Murine Hematopoietic Stem Cells that are Replicating In Vivo", J. Exp. Med., 183: 1797-1806 (1996).
Halder, Georg et al., "Transduction of mechanical and cytoskeletal cues by YAP and TAZ", Molecular Cell Biology, 13: 591-600 (2012).
Hall, Peter E. et al., "Laminin enhances the growth of human neural stem cells in defined culture media", BMC Neuroscience, 9: 71 (2008).
Hjelmeland, AB et al., "Acidic stress promotes a glioma stem cell phenotype", Cell Death and Differentiation, 18: 829-840 (2011).
Ihsan, Abu et al., "A phase diagram of neutral polyampholyte—from solution to tough hydrogel", J. Mater. Chem. B, 1: 4555-4562 (2013).
International Preliminary Report on Patentability issued in corresponding International Application No. PCT/JP2018/005884.
International Preliminary Report on Patentability issued in corresponding International Application No. PCT/JP2018/005884 [English translation].
International Search Report issued in corresponding International Application No. PCT/JP2018/005884.
Jabbari, Esmaiel et al., "Optimum 3D Matrix Stiffness for Maintenance of Cancer Stem Cells is Dependent on Tissue Origin of Cancer Cells", PLOS ONE, 10(7): e0132377, doi.10.1371/journal.pone.0132377 (2015).
Kemper, Kristel et al., "Molecular identification and targeting of colorectal cancer stem cells", Oncotarget, 1(6): 387-395 (2010).
Kwon, Hyuck Joon et al., "In vitro differentiation of chondrogenic ATDC5 cells is enhanced by culturing on synthetic hydrogels with various charge densities", Acta Biomaterialia, 6: 494-501 (2010).
Maeda, Eijiro et al., "Significant increase in Young's modulus of ATDC5 cells during chondrogenic differentiation induced by PAMPS/PDMAAm double-network gel: Comparison with induction by insulin", Journal of Biomechanics, 47: 3408-3414 (2014).
Pietras, Alexander et al., "Osteopontin-CD44 Signaling in the Glioma Perivascular Niche Enhances Cancer Stem Cell Phenotypes and Promotes Aggressive Tumor Growth", Cell Stem Cell, 14: 357-369 (2014).
Reynolds, Brent A. et al., "Generation of Neurons and Astocytes from Isolated Cells of the Adult Mammalian Central Nervous System", Science, 255: 1707-1710 (1992).
Sun, Tao Lin et al., "Physical hydrogels composed of polyampholytes demonstrate high toughness and viscoelasticity", Nature Materials, 12: 932-937 (2013).
Tsuda et al., Consortium of Biological Sciences (2017).
Uchida, Nobuko et al., "Direct isolation of human central nervous system stem cells", PNAS, 97(26): 14720-14725 (2000).
Yang, Jing Jing et al., "Hydrogels as feeder-free scaffolds for long-term self-renewal of mouse induced pluripotent stem cells", J Tissue Eng. Regen. Med., 9: 375-388 (2015).
Notice of Reasons for Refusal, dated Jan. 25, 2022, issued in corresponding Japanese Patent Application No. 2018-568662.

* cited by examiner

IF of Sox2 in KMG4 cells

Fig. 8B
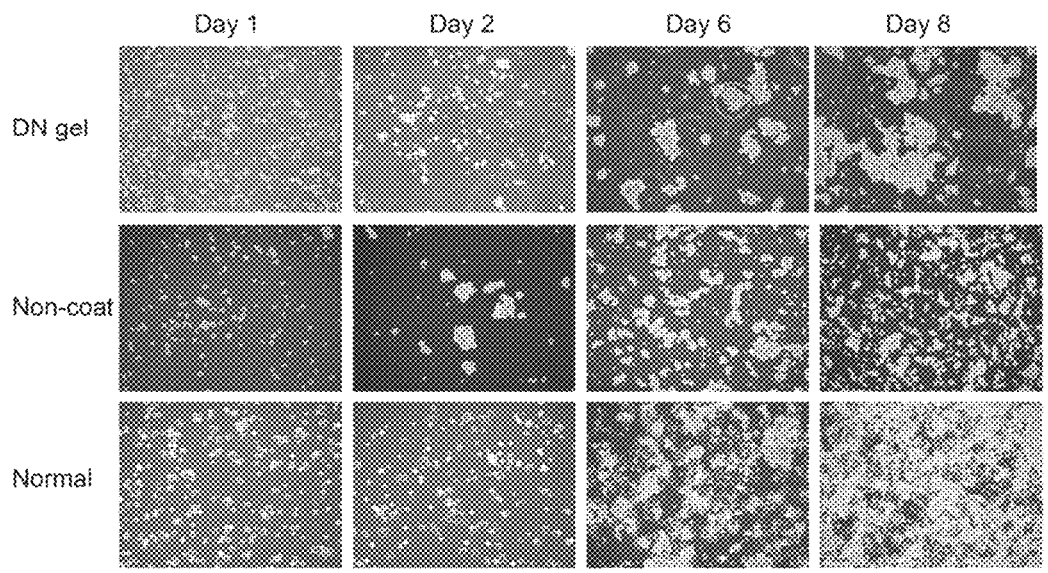
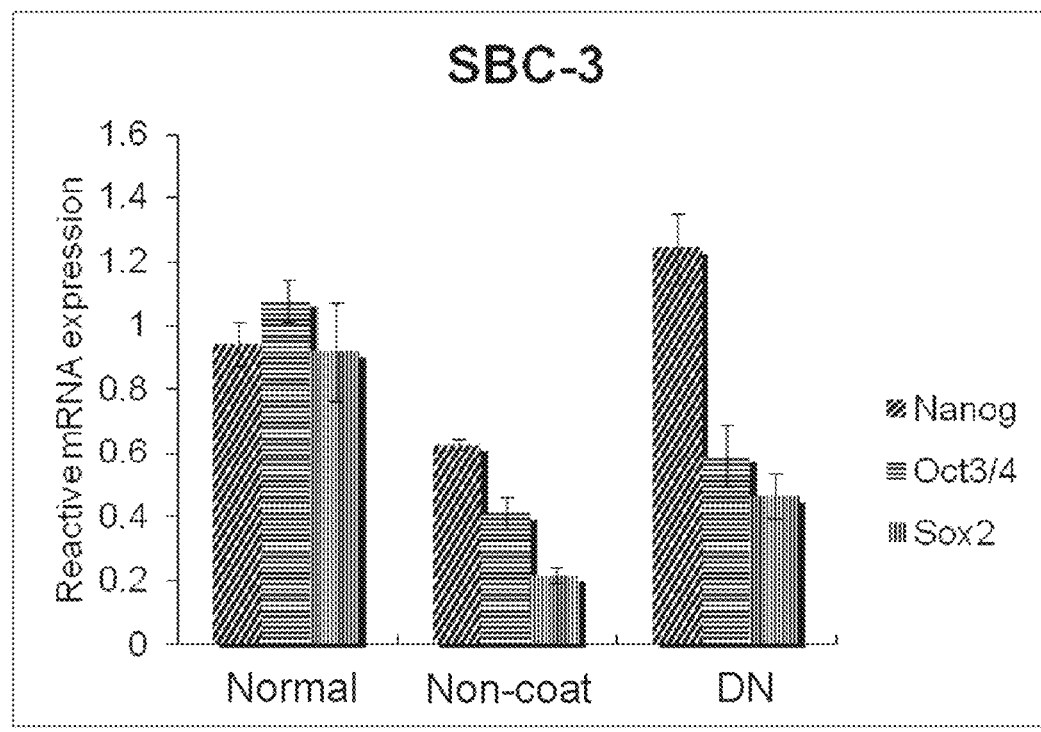

Fig. 15 KMG4 glioblastoma cells on DN, PCDME, and PNaSS gels

Fig. 19 Increased expression of *OPN* in KMG4 cells on DN, PCDME, and PNaSS gels Fig. 21
Increased expression of stemness markers in KMG4 cells on hydrogels
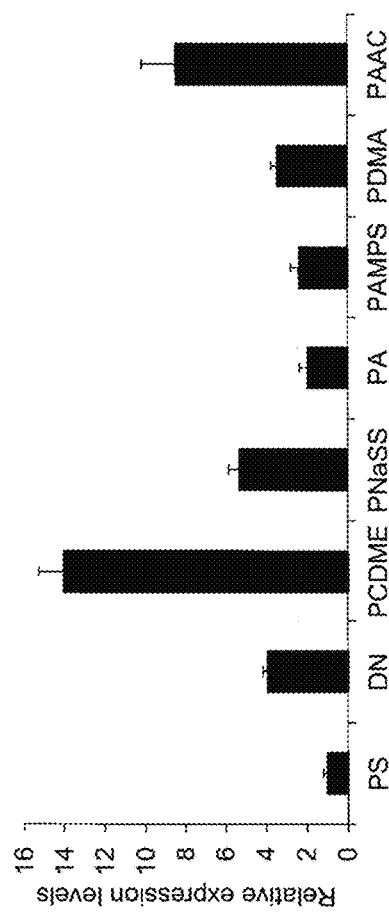
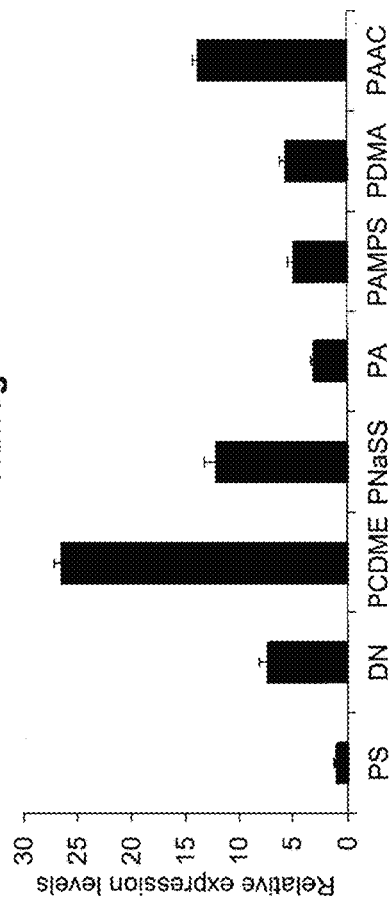

METHOD OF PRODUCING CANCER STEM CELLS

CROSS-REFERENCE TO RELATED APPLICATIONS

The present application is a §371 of International Application No. PCT/JP2018/005884, Feb. 20, 2018, which claims priority on the basis of from Japanese Patent Application No. 2017-28833 filed on 20 Feb. 2017. The entire disclosure of each of the aforesaid applications is incorporated by reference in the present application.

TECHNICAL FIELD

The present invention relates to a method of producing cancer stem cells.

BACKGROUND ART

Cancer stem cells are defined as cells having both a self-replicating ability and pluripotency, and it has been recently revealed that the cancer stem cell exhibits treatment resistance to radiation therapy, chemotherapy and molecular targeted therapy, and is a ca e of cancer relapse and metastasis. Since usually only an extremely small number of cancer stem cells are present in a tumor, it has been difficult to reveal and research the properties of cancer stem cells despite the importance thereof. Thus, in order to develop a definitive treatment targeted at cancer stem cells by elucidating the mechanism behind cancer relapse and metastasis as well as treatment resistance, it is extremely important to increase the ratio of cancer stem cells present among cancer cells and establish methods for the isolation and concentration thereof.

Methods have been developed in recent years for isolating and concentrating cancer stem cells.

(1) Isolation by spheroid formation: Spherical cell masses (spheroids) are formed by culturing cells while suspending in a serum-free medium followed by concentrating cancer stem cells (NPL 1).

(2) Isolation by side population fractionation: Based on data indicating that cancer stem cells are resistant to anticancer drugs, a DNA binding reagent is incorporated into the cells followed by isolating and acquiring a cell population having a potent ability to discharge that reagent by FACS (NPL 2).

(3) Isolation using cancer stem cell surface marker: Antibody to molecules specifically expressed on the surface of cancer stem cells is used to isolate and acquire cells expressing these molecules (NPL 3). For example, examples of colon cancer stem cell surface markers include LGR5, CD133, CD44, EpCAM, CD166, ALDH, CD24, CD26 and CD29.

(4) Isolation using glucose-free medium under hypoxic conditions: A cancer cell population containing cancer stem cells is cultured in medium that is substantially free of glucose under hypoxic conditions (NPL 4).

(5) Conventional technology for concentrating cancer stem cells in brain tumors: A technique referred to as a neurosphere assay is used. In addition to molecules of various types of cell growth factors and cytokines, this technique uses an extremely expensive culture broth that contains fetal bovine serum that is excluded in ordinary sphere formation assays (NPL 5). In addition, a technique is also used that uses laminin to isolate normal neural stem cells (NFL 6).

PATENT LITERATURE

[PTL 1] Japanese Patent Application Laid-open No. 2010-174063
[PTL 2] Japanese Patent Application Laid-open No. 2010-158180
[PTL 3] Japanese Patent Application Laid-open No. 2016-83276

NON-PATENT LITERATURE

[NPL 1] Science, 1992, 255, 1707-1710
[NPL 2] J. Exp. Med., 1996, 183, 1797-1806
[NPL 3] Oncotarget, 2010, 1, 387-395
[NPL 4] Cell Death Differ., 2011, 18, 829-840
[NPL 5] Proc. Natl. Acad. Sci. USA, 2000, 97, 15720-15725
[NPL 6] BMC Neurosci., 2008, 9, 71
[NPL 7] Stem Cells, 2015, 33, 1705-1718
[NPL 8] Genes Dev., 2011, 25, 2594-2609
[NPL 9] Nature, 2011, 474, 179-183
[NPL 10] Nat. Rev. Mol. Cell Biol., 2012, 13, 591-600
[NPL 11] Science, 344, 161-162, 2014
[NPL 12] Acta Biomaterialia, 6 (2010), 494-501
[NPL 13] Biomaterials, 26 (2005), 4588-4596
[NPL 14] Biomaterials, 28 (2007), 1752-1760
[NPL 15] J. Tissue Eng. Regen. Med., 2015, 9, 375-388
[NPL 16] Nature Materials, 2(10), 932-937, 2013
[NPL 17] Journal of Materials Chemistry B., 1(36), 4555-4562, 2013

The descriptions of PTL 1 to 3 and NPL 1 to 17 are incorporated herein in their entirety by reference.

SUMMARY OF INVENTION

Technical Problem

All of the above-mentioned methods have the problems of requiring expensive equipment, having high culturing costs, and requiring one week or more for culturing.

Therefore, an object of the present invention is to provide a means and method enabling the preparation of cancer stem cells without requiring expensive equipment, at comparatively inexpensive culturing costs, and in a comparatively short period of time, and to provide a means and method for such preparation of cancer stem cells.

Solution to Problem

The inventors of the present invention attempted a completely different approach from that of the prior art in order to provide a means and method for preparing cancer stem cells. Namely, the inventors of the present invention examined the culturing of cancer cells including human cancer stem cells using a synthetic polymer gel developed and produced by Jian Ping Gong, one of the present inventors (PTL 1). As a result, the inventors of the present invention found that, as a result of using a portion of that synthetic polymer gel, cancer stem cells included in cancer cells are cultured preferentially in comparison with other cancer cells and cancer cells can be obtained that have an increased concentration of cancer stem cells, thereby leading to completion of the present invention.

The present invention is as described below.

[1] A method of producing cancer stem cells, comprising: culturing a living cell population containing cancer cells in the presence of a gel substance to obtain a living cell population containing cancer stem cells, wherein the gel substance is a material that induces expression of osteopontin in at least a portion of cells contained in the living cell population.

[2] The production method according to [1], wherein the gel substance is a synthetic polymer gel composed of double network gel, PNaSS gel, PCDME gel, PA gel, PAMPS gel, PDMA gel or PAAc gel.

[3] The method according to [1], wherein the living cell population containing cancer stem cells contains cells exhibiting a spherical shape.

[4] The method according to any one of [1] to [3], wherein cells in the living cell population containing cancer stem cells have a higher expression level of Oct3/4, Sox2 and/or Nanog than that prior to culturing in the presence of the gel substance.

[5] A method for testing the strength of the tendency for cancer cells to convert to cancer stem cells, comprising:
culturing a living cell population containing cancer cells in the presence of a gel substance, and
measuring the quality and/or quantity of cancer stem cells in the resulting culture medium; wherein
the gel substance is a material that induces expression of osteopontin in at least a portion of the cells contained in the living cell population.

[6] The method according to [5], wherein the living cell population containing cancer cells is at least a portion of collected tissue containing cancer.

[7] The method according to [5] or [6], wherein the gel substance is a synthetic polymer gel composed of double network gel, PNaSS gel, PCDME gel, PA gel, PAMPS gel, PDMA gel or PAAc gel.

[8] A method of testing an effect of a test substance on cancer stem cells, comprising:
culturing a living cell population containing cancer cells and/or cancer stem cells in the presence of a test substance and a gel substance; wherein
the gel substance is a material that induces expression of osteopontin in at least a portion of the cells contained in the living cell population.

[9] The method according to [8], wherein the culturing is carried out in vivo or in vitro.

[10] The method according to [8] or [9], wherein the living cell population containing cancer stem cells is a living cell population obtained by culturing a living cell population containing cancer cells in the presence of the gel substance.

[11] The method according to any one of [8] to [10], wherein the gel substance is a synthetic polymer gel composed of double network gel, PNaSS PCDME gel, PA gel, PAMPS gel, PDMA gel or PAAc gel.

[12] An agent for inducing conversion of cancer cells to cancer stem cells, containing a gel substance that induces expression of osteopontin in at least a portion of cells contained in a living cell population.

[13] The agent for inducing conversion according to [12], wherein the gel substance is a synthetic polymer gel composed of double network gel, PNaSS gel, PCDME gel, PA gel, PAMPS gel, PDMA gel or PAAc gel.

[14] The agent for inducing conversion according to [12] or [13], wherein the gel substance is in the form of a sheet or particles.

[15] A kit for inducing conversion of cancer cells to cancer stem cells comprising the following (1) and (2):
(1) a gel substance that induces expression of osteopontin in at least a portion of the ells contained in a living cell population, and
(2) a culture broth for culturing cancer cells.

[16] The kit according to [15], wherein the gel substance is a synthetic polymer gel composed of double network gel, PNaSS gel, PCDME gel, PA gel, PAMPS gel, PDMA gel or PAAc gel.

[17] The kit according to [15] or [16], wherein the gel substance is in the form of a sheet or particles.

Advantageous Effects of Invention

According to the present invention, cancer cells having an increased concentration of cancer stem cells can be obtained by culturing cancer cells using a specific synthetic polymer gel as a scaffold. In the present invention, ordinary culture medium (such as DMEM containing 10% fetal bovine serum) is the only reagent required other than the synthetic polymer gel and special equipment is not required. Moreover, expression of stem cell marker molecules can be induced in a short period of time such as one day.

Consequently, as a result of using the present invention, cancer cells having an increased concentration of cancer stem cells can be prepared from cancer cells collected from a cancer patient, and by using these cancer cells having an increased concentration of cancer stem cells, the properties of stem cells during relapse can be predicted at the time of the initial cancer diagnosis, for example. Moreover, this enables a diagnosis to be made for administering a therapeutic drug for preventing relapse. In addition, the characteristics of cancer stem cells and applicable therapeutic drugs can be predicted in the case of having relapsed prior to a cancer patient receiving molecular targeted therapy. The present invention can serve as the foundation for the development of novel testing methods for selecting cancer treatment drugs.

BRIEF DESCRIPTION OF DRAWINGS

FIG. 8B indicates photographs of cells after culturing a lung cancer cell line (SBC3) and the results of confirming induction of expression of stem cell markers (Sox2, Nanog, Oct3/4 mRNAs) by qRT-PCR in Example 1(1).

FIG. 21 indicates the results of confirming induction of expression of stem cell marker molecules (Oct3/4, Nanog mRNAs) in KMG4 cells cultured on four types of polymer gels (PA, PAMPS, PDMA and PAAc gels) by qRT-PCR along with the results in cells cultured in DN, PCDME and PNaSS gels in Example 4.

DESCRIPTION OF EMBODIMENTS

Method for Producing Cancer Stem Cells

A first aspect of the present invention relates to a method of producing cancer stem cells.

This production method comprises obtaining a living cell population containing cancer stem cells by culturing a living cell population containing cancer cells in the presence of a gel substance. Moreover, the gel substance is a material that induces expression of osteopontin in at least a portion of the cells contained in the living cell population.

In the method of producing cancer stem cells of the present invention, a living cell population containing cancer cells is used as a starting material, this cell population is cultured in the presence of a gel substance, and a living cell population containing cancer stem cells is obtained as the resulting culture.

The living cell population containing cancer cells used as a starting material can be, for example, a specimen (tissue section) from a body containing cancer cells collected from a cancer patient and primary cultured cancer cells The culture medium and culture conditions are the same as those of culturing conventionally used to culture cancer cells with the exception of culturing in the presence of a gel substance. For example, ordinary culture medium (such as DMEM containing 10% fetal bovine serum) can be used as culture medium, and culturing can be carried out by, for example, seeding the cells at a cell density of $1 \times 10^5$/mL for 24 hours at 37° C. in a 5% $CO_2$ environment. Culturing can be carried out in a state in which the cells are able to contact the surface of the gel substance, and more specifically, can be carried out on a sheet-like gel substance. However, culturing is not limited to that carried out on a sheet-like gel substance, but rather any method can be used provided culturing is carried out in a state in which the cells are able to contact with the surface of the gel substance. For example, a particulate gel substance can be used and culturing can be carried out while allowing a culture medium having the particulate gel substance dispersed therein to stand undisturbed or while stirring.

In the present invention, the above-mentioned gel substance is selected from materials that induce expression of osteopontin in at least a portion of the cells contained in the living cell population. Such a gel substance can be, for example, a synthetic polymer gel composed of double network gel (DN gel), PNaSS gel, PCDME gel, PA gel, PAMPS gel, PDMA gel or PAAc gel. However, these examples are not intended to be limiting, but rather the gel substance can be any material that induces expression of osteopontin in at least a portion of the cells contained in the living cell population.

Figure 12:
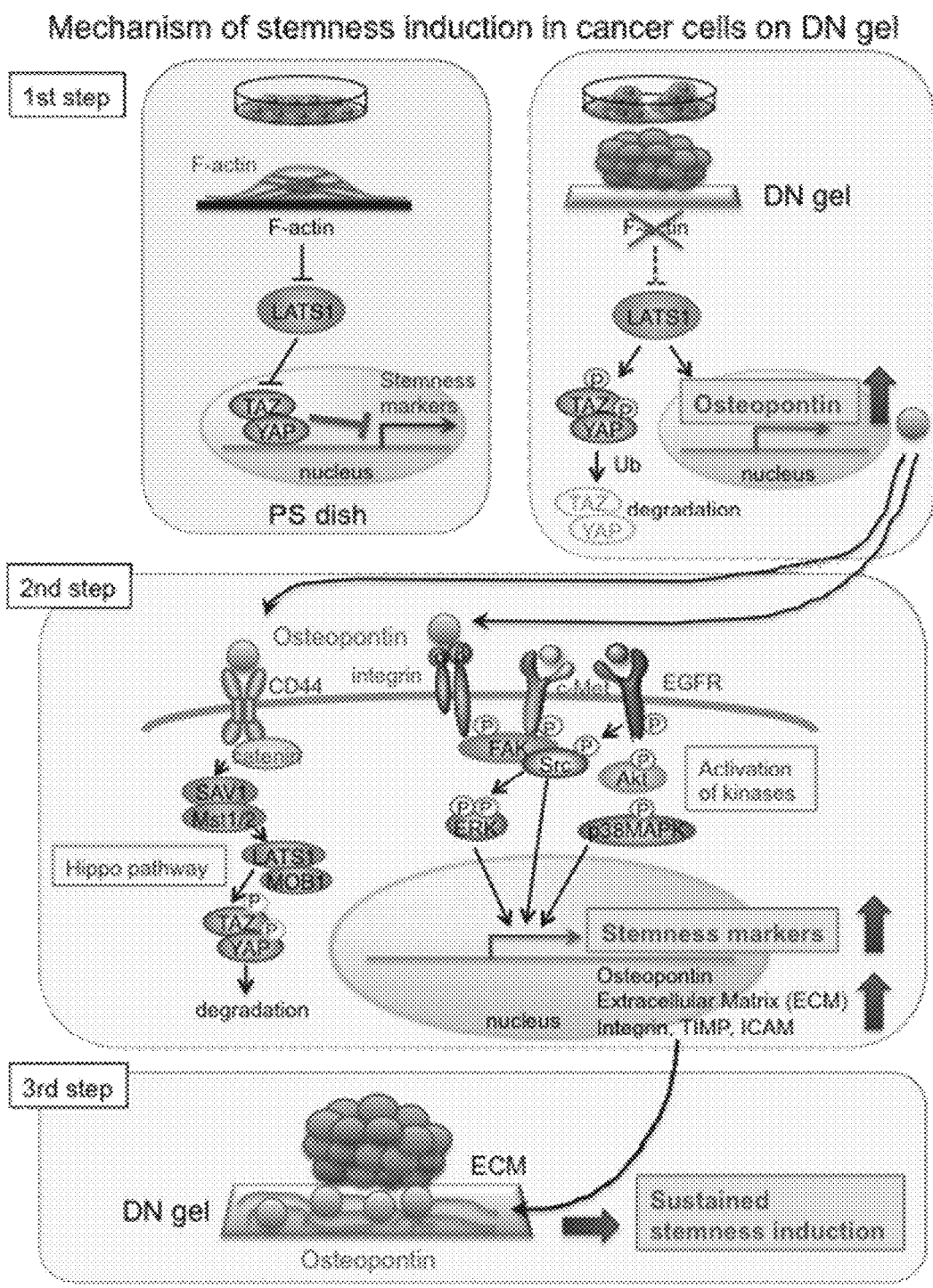
FIG. 12 is a schema of the mechanism behind induction of cancer stemness from cancer cells.

As described in detail in Example 1(2), induction of expression of a brain tumor stem cell marker in cells obtained by culturing a living cell population containing cancer cells that have been cultured on a synthetic polymer gel in the present invention was determined to be caused by induction of the expression of osteopontin in cells cultured on the synthetic polymer gel. Cancer cells have receptors for osteopontin such as CD44 or integrin (ITG) on the surface thereof, and the Hippo pathway has been determined to be activated from the osteopontin/CD44 signal pathway while cell adhesion molecules including FAK and various types of kinase groups including Src, Akt, ERK and p38MAPK have been determined to be activated from the osteopontin/ITG pathway (NPL 7). As shown in FIG. 12, osteopontin for which expression has been induced (first step) was indicated as activating the Hippo pathway and various kinase groups via osteopontin receptors on the surface of cancer cells and accelerating the expression of Oct3/4, Sox2 and Nanog, while expression of stem cell markers was determined to be suppressed downstream from the Hippo pathway in brain tumor cells.

Furthermore, in glioblastoma, a TAZ (transcriptional coactivator), which is a transducer of the Hippo pathway, is known to be important in the acquisition of cancer stemness (NPL 8), while YAP/TAZ has been reported to be important as a sensor of mechanical stimulation (mechanotransduction) (NPL 9 and NPL 10). On the basis thereof, by culturing a living cell population containing cancer cells in a state that enables contact with a specific synthetic polymer gel, the cancer cells are stimulated by the synthetic polymer gel, acquire cancer stemness, and the concentration of cancer stem cells in the living cell population is presumed to increase.

In the present invention, the above-mentioned gel substance is selected from materials that induce expression of osteopontin in at least a portion of the cells contained in a living cell population. Examples of gel substances having such a property include synthetic polymer gels composed of double network gel (DN gel), PNaSS gel, PCDME gel, PA gel, PAMPS gel, PDMA gel and PAAc gel. In these synthetic gels, as indicated by the results of Example 2(1) and Example 4, induction of expression of osteopontin (OPN) mRNA in KMG4 cells cultured on these synthetic gels was able to be confirmed by qRT-PCR. In the present invention, whether or not the gel substance is a material that induces expression of osteopontin in at least a portion of the cells contained in the living cell population can be determined by confirming induction of the expression of osteopontin (OPN) mRNA in any one type of cell contained in the above-mentioned living cell population by qRT-PCR.

Examples of double network gel (DN gel) include the following two types of gels.

(i) Gel having an interpenetrating network structure composed of a first network structure (A) and a second network structure (B) formed within the first network structure (A).

(ii) Gel having an interpenetrating network structure composed of a first network structure (A) and a polymer (B') formed within the first network structure (A).

An example of a double network gel is the gel described in PTL 1, and a specific example thereof is a gel having an interpenetrating network structure composed of RAMPS (poly(AMPS)) as the first network structure (A) and PDMA as the second network structure (B) formed within the first network structure (A). Poly(AMPS) and RAMPS are abbreviations for poly(2-acrylamido-2-methyl-1-propanesulfonic acid), while PUMA is the abbreviation for poly(N,N-dimethylacrylamide). NPL 11 can be referred to regarding double network gel.

PNaSS gel is a gel composed of poly(sodium p-styrene sulfonate) (PNaSS) and examples thereof are described in PTL 2, NPL 13 and NPL 14. More specifically, PNaSS gel can be prepared by polymerizing sodium p-styrene sulfonate with a crosslinking agent. Examples of crosslinking agents include compounds similar to crosslinking agents able to be used with PCDME gel to be subsequently described such as methylenebisacrylamide.

PCDME gel is a gel that contains poly-N-(carboxymethyl-N,N-dimethyl-2-(methacryloyloxy) ethanaminium (PCDME), and an example thereof is described in PTL 3. More specifically, PCDME is a gel compound that contains PCDME as the main chain thereof in which this main chain is crosslinked with a crosslinking agent. PCDME can be prepared by polymerizing a carboxymethylbetaine monomer, which is a monomer component of PCDME, with a crosslinking agent. At least one crosslinking agent is selected from the group consisting of, for example, methylenebisacrylamide, methylenebismethacrylamide, butanediol diacrylate, butanediol dimethacrylate, ethylene glycol diacrylate, ethylene glycol dimethacrylate, allyl (meth)acrylate, triallyl cyanurate, diallyl maleate, polyallyl ester, tetraallyloxyethane, triallylamine, tetraallylethylenediamine, pentaerythritol triallyl ester and ethylenebisacrylamide.

PA gel is the abbreviation for polyampholyte gel and is a polymer having both acidic and basic functional groups. An example of the acidic group is sulfonic acid, while an example of the basic group is an ammonium group (aminium group). This polymer can be synthesized by using a monomer having sulfonic acid group or a salt thereof (such as styrene suifonic acid, vinyl sulfonic acid, 2-acrylamido-2-methylpropane sulfonic acid, ethylene sulfonic acid, 2-methacryloxyethane-1-sulfonic acid, 3-methacryloxyethane-1-sulfonic acid, 3-(vinyloxy)propane-1-sulfonic acid or derivatives thereof) and a monomer having an ammonium group (aminium group) (such as diallyl dimethyl ammonium, 2-butyl-methacryloxyethyl trimethyl ammonium, 4-vinylbenzotrimethyl ammonium, butyl acrylate methacryloxyethyl trimethyl ammonium, or derivatives thereof) followed by copolymerizing these monomers. Examples thereof are described in NPL 16 and NPL 17.

In the examples, sodium p-styrene sulfonate and [3-(methacryloylamino)propyl]trimethylaminium chloride were used to synthesize a copolyrner gel by using oxoglutaric acid as a polymerization initiator. This gel is referred to as PA gel in the examples.

RAMPS gel is a gel composed of poly(2-acrylamido-2-methyl-1-propanesulfonic acid). It is also an example of a constituent polymer of the above-mentioned double network gel. RAMPS gel is a copolymer gel synthesized by using sodium acrylamidomethylpropane sulfonate and methylenebisacrylamide as monomers and using oxoglutaric acid as a polymerization initiator. Examples thereof are described in NPL 12 to NPL 15.

PDMA gel is a gel composed of poly(N,N'-dimethylacrylamide). In the examples, PDMA gel is a copolymer gel synthesized by using dimethylacrylamide and methylenebisacrylamide as monomers and using oxoglutaric acid as a polymerization initiator. An example thereof is described in NPL 15.

PAAc gel is a gel composed of poly(acrylic acid). In the examples, PAAc gel is a copolymer gel synthesized by using acrylic acid and methylenebisacrylamide as monomers and using oxoglutaric acid as a polymerization initiator, Examples thereof are described in NPL 12 and NPL 13.

In the method of the present invention, a living cell population containing cancer stem cells can be obtained as a culture without the use of special means with the exception of culturing in the presence of the gel substance. Whether or not the cells contained in the living cell population are cancer stem cells can be determined according to, for example, the morphology of the cells or the expression level of Oct3/4, Sox2 and/or Nanog. With respect to morphology, cancer stem cells can be cells that exhibit, for example, a spherical structure. However, there are cases in which cells may be cancer stem cells despite not exhibiting a spherical structure (see Example 2). In addition, cells demonstrated increased expression levels of one or two or more of any of Oct3/4, Sox2 and/or Nanog can also be selected as cancer stem cells.

Cancer cells in addition to cancer stem cells may be contained in the living cell population containing cancer stem cells as a culture.

Method for Testing Strength of Tendency for Cancer Cells to Convert to Cancer Stem Cells A second aspect of the present invention is a method for testing the strength of the tendency for cancer cells to convert to cancer stem cells. This method comprises culturing a living cell population containing cancer cells in the presence of a gel substance and measuring the quality and/or quantity of cancer stem cells present in the resulting culture medium. The gel substance is a material that induces expression of osteopontin in at least a portion of the cells contained in the above-mentioned living cell population, and is the same material as the material explained in the previously described first aspect.

In the second aspect (method) of the present invention, a living cell population containing cancer cells is cultured in the presence of a gel substance. The living cell population containing cancer cells can be at least a portion of collected tissue that contains cancer.

As explained in the first aspect, the gel substance may be in the form of a sheet or particles. The culture method and culture conditions during culturing in the presence of the gel substance are basically the same as those explained in the first aspect.

The quality and/or quantity of cancer stem cells in the resulting culture medium are measured. Measurement of the quality and/or quantity of cancer stem cells can be carried out by, for example, observing the appearance of cancer stem cells in the culture medium (observing for the presence of spherical cells or counting the number of spherical cells) or measuring the expression levels of one or two or more of any of Oct3/4, Sox2 and/or Nanog in the cancer stem cells present in the culture medium.

The strength of the tendency for cancer cells to convert to cancer stem cells can be determined from the results obtained. The potential for relapse of collected tissue containing cancer can be diagnosed by medical professionals based on this result.

Method for Testing Effect of Test Substance on Cancer Stem Cells

A third aspect of the present invention relates to a method for testing the effect of a test substance on cancer stem cells. This method comprises culturing a living cell population containing cancer cells and/or cancer stem cells in the presence of a test substance and a gel substance. The gel substance is a material that induces expression of osteopontin in at least a portion of the cells contained in the above-mentioned living cell population, and is the same material as that explained in the previously described first aspect.

The third aspect (method) of the present invention makes it possible to evaluate, for example, the effect of a test substance on cancer stem cells such as the suppression or promotion of growth of cancer stem cells, and as a result thereof, drugs can be screened that are able to suppress the growth of cancer stem cells.

As explained in the first aspect, the gel substance may be in the form of a sheet or particles. The culture method and culture conditions during culturing in the presence of the gel substance are basically the same as those explained in the first aspect with the exception of the presence or absence of the test substance. In addition, culturing can be carried out in vivo or in vitro. A test substance having an effect on the growth of cancer stem cells can be easily screened by carrying out culturing in vitro. In addition, an effect of a test substance in the body on cancer stem cells can be determined more directly by testing in vivo.

The living cell population containing cancer stem cells used in the third aspect (method) of the present invention is a living cell population obtained by, for example, culturing a living cell population containing cancer cells in the presence of a gel substance in the method of the first aspect.

Agent for Inducing Conversion of Cancer Cells to Cancer Stem Cells

A fourth aspect of the present invention relates to an agent for inducing conversion of cancer cells to cancer stem cells that contains a gel substance that induces expression of osteopontin in at least a portion of the cells contained in a living cell population.

As previously described, the gel substance that induces expression of osteopontin in at least a portion of the cells contained in the living cell population is able to induce conversion of cancer cells to cancer stem cells as a result thereof. Therefore, the present invention provides an agent containing this gel substance that can be used to induce conversion of cancer cells to cancer stem cells.

The gel substance can be a synthetic polymer gel composed of, for example, double network gel, PNaSS gel, PCDME gel, PA gel, PAMPS gel, PDMA gel or PAAc gel. Although the gel substance used as an agent for inducing conversion of cancer cells to cancer stem cells can be in the form of, for example, a sheet or particles, the form is not intended to be limited thereto. The gel substance may be of any form provided it is a form that is suitable for inducing conversion of cancer cells to cancer stem cells.

Kit for Inducing Conversion of Cancer Cells to Cancer Stem Cells

A fifth aspect of the present invention relates to a kit for inducing conversion of cancer cells to cancer stem cells that contains the following (1) and (2):

(1) gel substance that induces expression of osteopontin in at least a portion of the cells contained in a living cell population, and (2) culture medium for culturing cancer cells.

The gel substance as (1) is a material that induces expression of osteopontin in at least a portion of the cells contained in a living cell population and is the same as that explained in the first and fourth aspects. The gel substance is a synthetic polymer gel composed of double network gel, PNaSS gel, PCDME gel, PA gel, PAMPS gel, PDMA gel or PAAc gel.

The culture medium for culturing cancer cells as (2) be a culture medium typically used to culture a living cell population containing cancer cells, which is the object of culturing, or a culture medium suitable for culturing a living cell population containing cancer cells.

EXAMPLES

The following provides a more detailed explanation of the present invention based on examples thereof. However, the examples are only intended to be exemplary and the present invention is not limited thereto.

The synthesis methods, initial elastic moduli and degrees of swelling of the synthetic polymer double network (DN) gel, PCDME gel, PNaSS gel, PA gel, PAMPS gel, PDMA gel and PAAc gel used in the examples are as indicated below.

(1) DN gel: Gel obtained by polymerizing PAMPS (poly (AMPS): poly(2-acrylamido-2-methyl-1-propanesulfonic acid)) as the first network with PDMA (poly(N,N-dimethylacrylamide)) as the second network. 2.1 g of sodium acrylamidomethylpropanesulfonate, 0.062 g of methylenebisacrylamide and 0.015 g of oxoglutaric acid were dissolved with pure water to obtain 10 mL of an aqueous solution using a 10 mL volumetric flask. This was poured into a glass mold measuring 8 cm×8 cm×0.5 mm and irradiated with ultraviolet light for 8 hours in an argon atmosphere to synthesize a gel having a first network. This gel was divided into four portions, and when placed in 500 mL of an aqueous solution containing 99 g of N,N'-dimethylacrylamide, 0.15 g of methylenebisacrylamide and 0.15 g of oxoglutaric acid, the aqueous solution was absorbed and the gel swelled to about 10 times the volume thereof. The swollen gel was placed between glass plates and irradiated with ultraviolet light for 8 hours in an argon atmosphere to synthesize a second network. The gel having these two types of synthesized networks was placed in pure water, the pure water was replaced three times, and unreacted raw materials were removed to obtain DN gel. The initial elastic modulus of the DN gel was 0.435 MPa and the degree of swelling was 7.3 g/g.

(2) PCDME: Poly-N-(carboxymethyl)-N,N-dimethyl-2-(methacryloyloxy) ethanaminium. 6.5 g of carboxymethylbetaine monomer, 0.19 g of methylenebisacrylamide and 0.0044 g of oxoglutaric acid were dissolved with pure water to obtain 30 mL of an aqueous solution using a 30 mL volumetric flask. This was poured into a glass mold measuring 8 cm×8 cm×1 mm and irradiated with ultraviolet light for 8 hours in an argon atmosphere to synthesize a gel. The synthesized gel was placed in pure water, the pure water was replaced three times and unreacted raw materials were removed to obtain PCDME gel, The initial elastic modulus of the PCDME gel was 0.0507 MPa and the degree of swelling was 8.6 g/g.

(3) PNaSS: Poly(sodium p styrene sulfonate). 2.1 g of sodium p-styrene sulfonate, 0.062 g of methylenebisacrylamide and 0.0015 g of oxogiutaric acid were dissolved with pure water to obtain 10 mL of an aqueous solution using a 10 mL volumetric flask. This was poured into a glass mold measuring 8 cm×8 cm×0.5 mm and irradiated with ultraviolet light for 8 hours in an argon atmosphere to synthesize a gel. The gel was placed in pure water, the pure water was replaced three times, and unreacted raw materials were removed to obtain PNaSS gel. The initial elastic modulus of the PNaSS gel was 0.0026 MPa and the degree of swelling was 306.8 g/g.

(4) PA: Polyampholyte. 6.2 g of sodium p-styrene sulfonate, 6.0 g of [3-(methacryloylamino)propyl] trimethylaminium•chloride and 0.0083 g of oxoglutaric acid were dissolved with pure water to obtain 10 mL of an aqueous solution using a 30 mL volumetric flask. This was poured into a glass mold measuring 8 cm×8 cm×1 mm and irradiated with ultraviolet light for 10 hours in an argon atmosphere to synthesize a gel. This was placed in pure water, the pure water was replaced three times and unreacted raw materials were removed to obtain PA gel.

(5) RAMPS: Poly(2-acrylamide-2-methyl-1-propane-sulfonic acid). 2.1 g of sodium acrylamidomethylpropane sulfonate, 0.062 g of methylenebisacrylamide and 0.015 g of oxoglutaric acid were dissolved with pure water to obtain 10 mL of an aqueous solution using a 10 mL volumetric flask. This was poured into a glass mold measuring 8 cm×8 cm×0.5 mm and irradiated with ultraviolet light for 8 hours in an argon atmosphere to synthesize a gel. The synthesized gel was placed in pure water, the pure water was replaced three times and unreacted raw materials were removed to obtain PAMPS gel.

(6) PUMA: Poly(N,N'-dimethylacrylamide). 3.3 g of dimethylacrylamide, 0.19 g of methylenebisacrylamide and 0.044 g of oxoglutaric acid were dissolved with pure water to obtain 30 mL of an aqueous solution using a 30 mL volumetric flask. This was poured into a glass mold measuring 8 cm×8 cm×1 mm and irradiated with ultraviolet light for 8 hours in an argon atmosphere to synthesize a gel. The synthesized gel was placed in pure water, the pure water was replaced three times and unreacted raw materials were removed to obtain PUMA gel.

(7) PAAc: Poly(acrylic acid). 2.2 g of acrylic acid, 0.19 g of methylenebisacrylamide and 0.044 g of oxoglutaric acid were dissolved with pure water to obtain 30 mL of an aqueous solution using a 30 mL volumetric flask. This was poured into a glass mold measuring 8 cm×8 cm×1 mm and irradiated with ultraviolet light for 8 hours in an argon atmosphere to synthesize a gel. The synthesized gel was placed in pure water, the pure water was replaced three times and unreacted raw materials were removed to obtain PAAc Gel.

Example 1(1)

Analysis of Induction of Expression of Brain Tumor Stem Cell Marker Molecules by Synthetic Polymer DN Gel Human glioblastoma cell lines (KMG4, U138, U343), human primary glioblastoma cells (G137, G140, G144, G150), lung cancer cell lines (H209, SBC3) and ovarian cancer cell lines (KF28, Tu-OM-1) were seeded on synthetic polymer DN gel at $1\times10^5$/mL followed by culturing.

Figure 1:
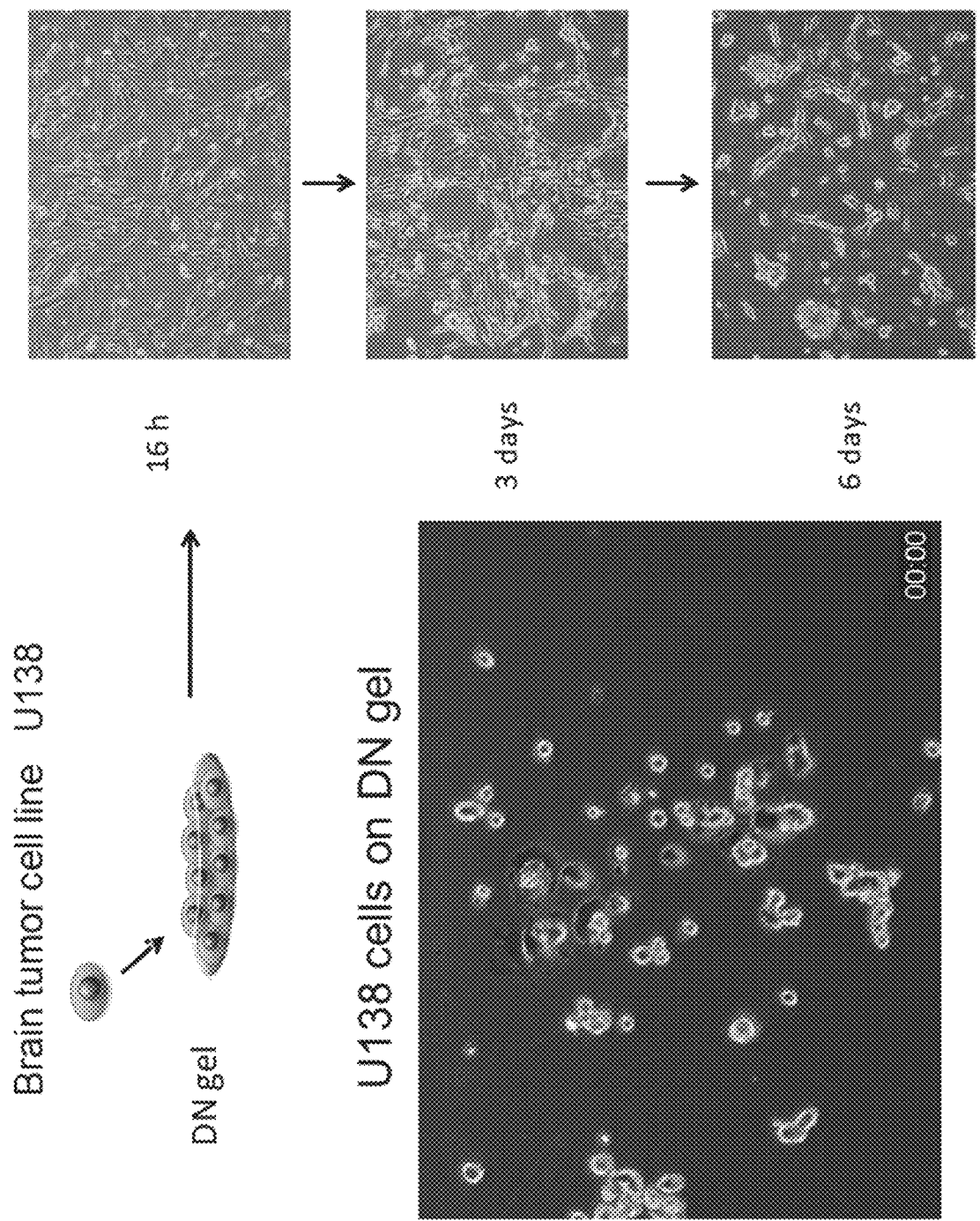
FIG. 1 indicates photographs of cells of a glioblastoma cell line (U138) on DN gel 16 hours, 3 days and 6 days in Example 1(1).
Figure 2:
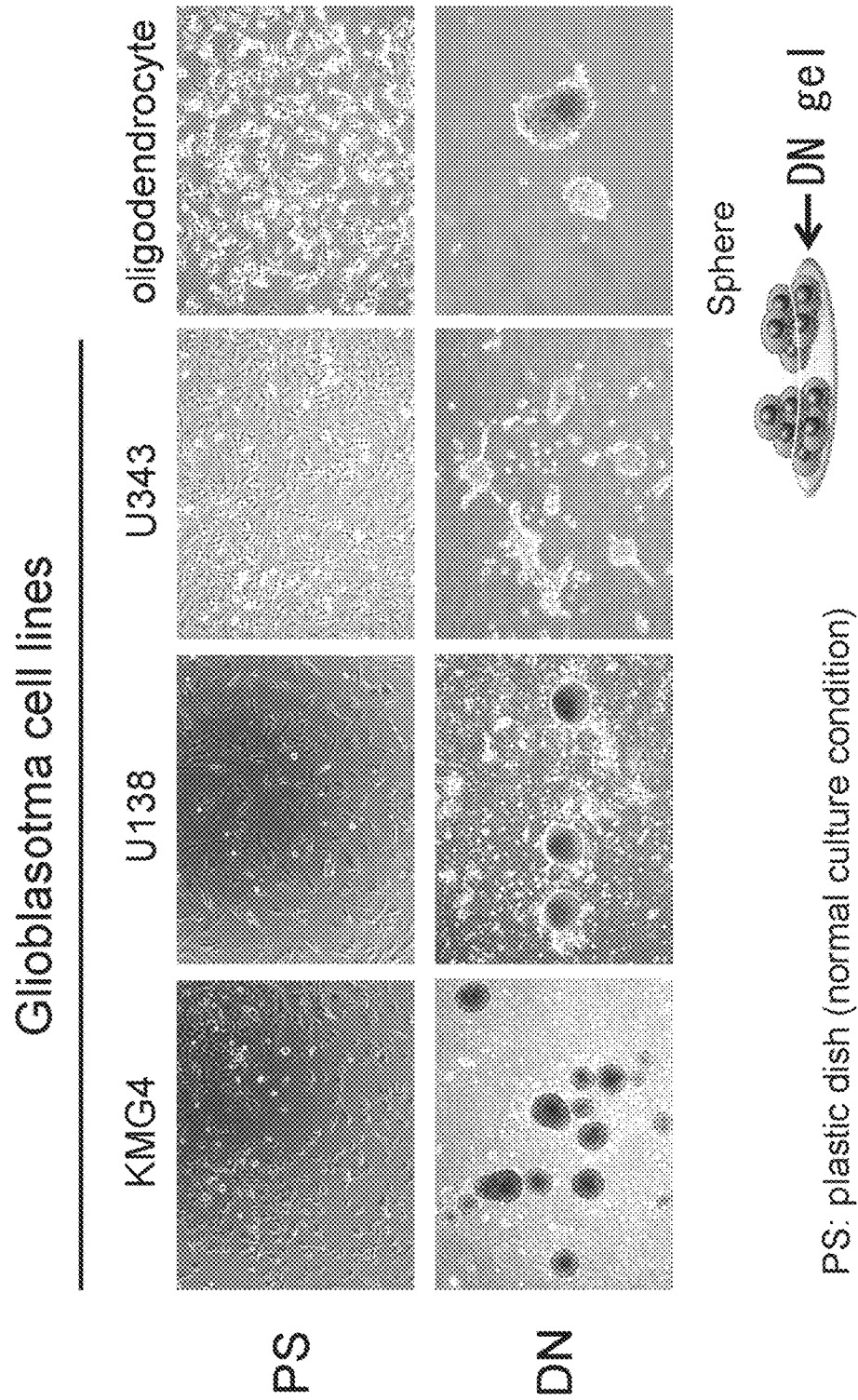
FIG. 2 indicates photographs of a glioblastoma cell line (KMG4) and oligodendrocytes after culturing for 8 days along with photographs of cells of glioblastoma cell lines (U136, U343) after culturing for 21 days (sphere formation) in Example 1(1) (PS: polystyrene culture dish, DN: DN gel).
Figure 3:
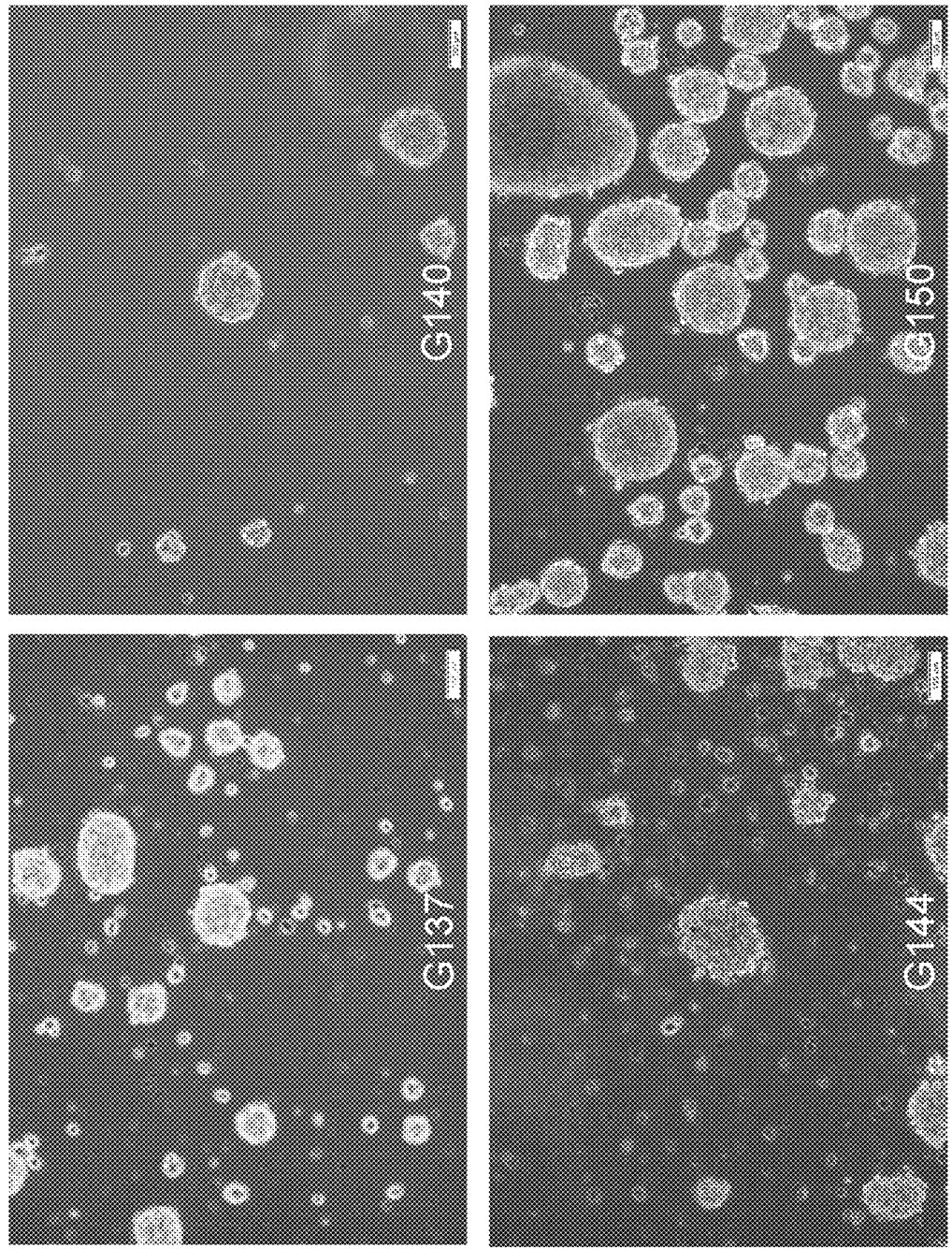
FIG. 3 indicates photographs of primary cells of glioblastoma cell lines (G137, G140, G144, G150) after culturing for 24 hours on DN gel (sphere formation) in Example 1(1).
Figure 4:
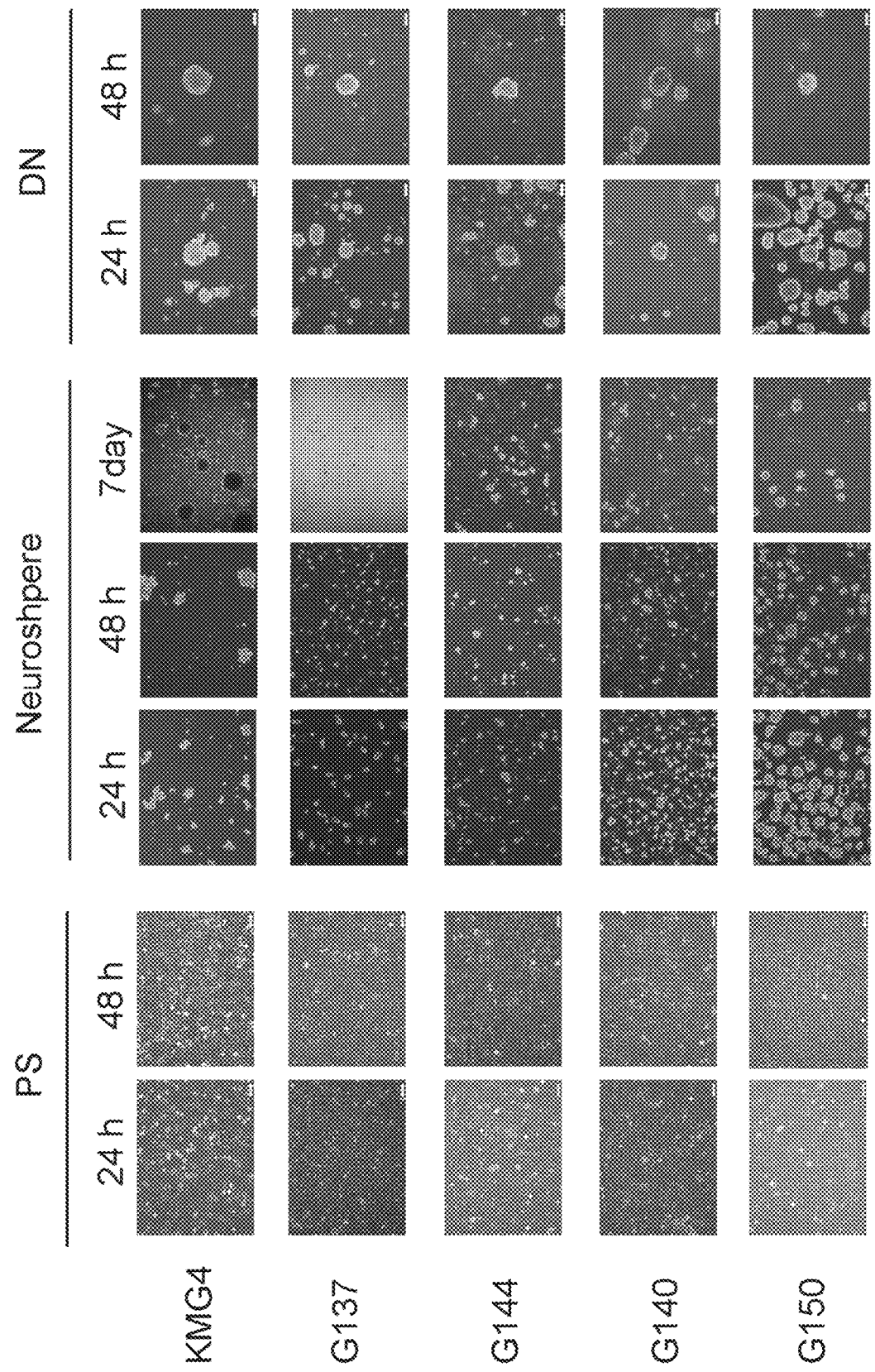
FIG. 4 indicates photographs of cells of brain tumor cell lines KMG4, G137, G140, G144 and G150 after culturing for 24 hours and 48 hours in Example 1(1).

Photographs of U138 cells after 16 hours, 3 days and 6 days are shown in FIG. 1. Moreover, photographs of KMG4 and oligodendrocyte cells after culturing for 8 days, photographs of U138 and U343 cells after culturing for 21 days, and photographs of G137, G140, G144 and G150 cells after culturing for 24 hours are shown in FIG. 2 and FIG. 3, respectively, Moreover, photographs of KMG4, G137, G140, G144 and G150 cells after 24 hours and 48 hours are shown in FIG. 4.

Figure 5:
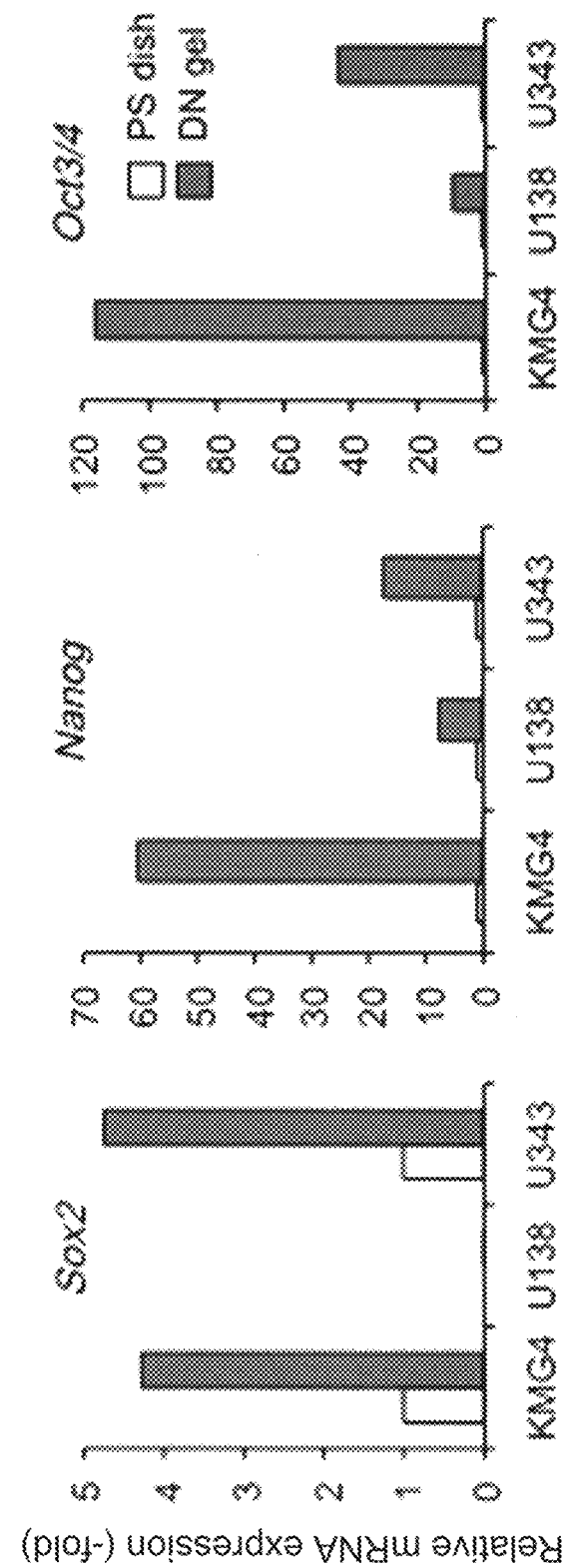
FIG. 5 indicates the results of confirming induction of expression of Sox2, Nanog and Oct3/4 mRNAs by qRT-PCR after culturing KMG4, U138 and U343 for 3 days in Example 1(1).
Figure 6:
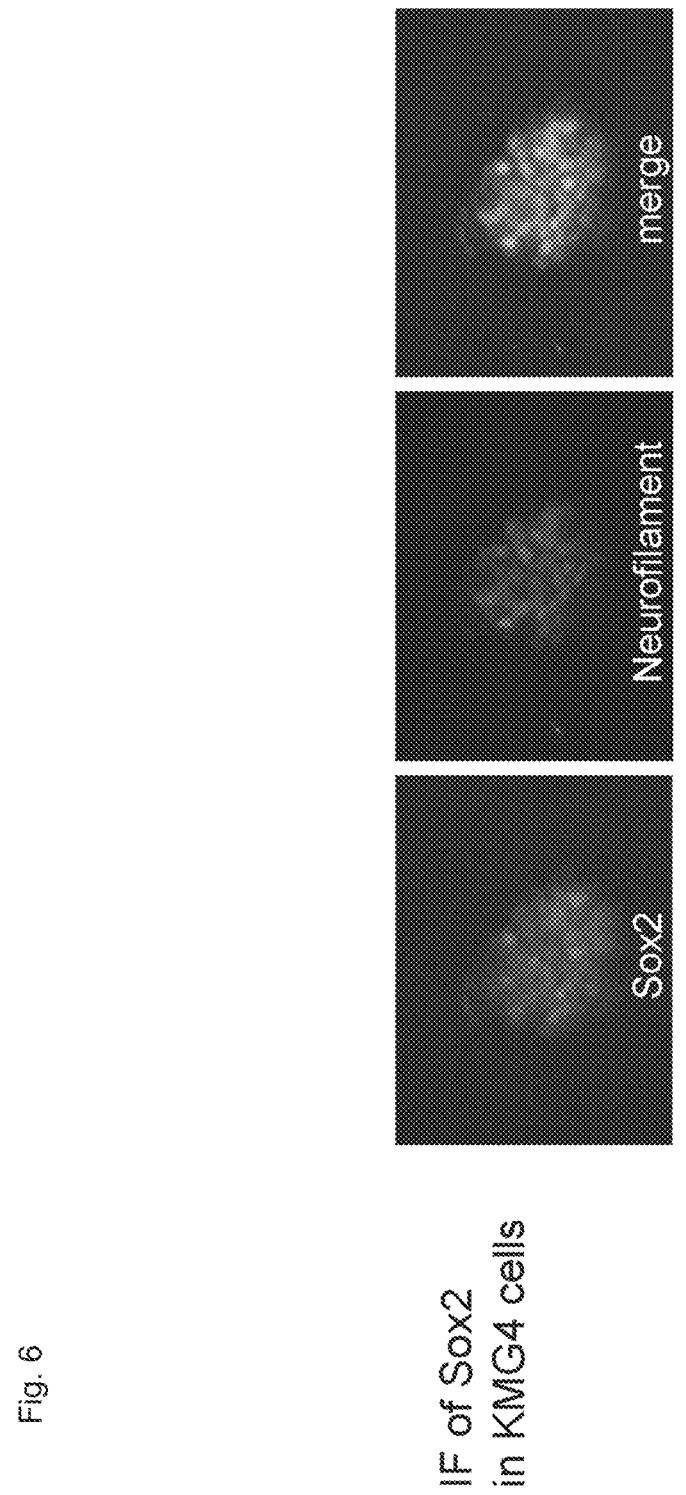
FIG. 6 indicates the results of confirming induction of expression of Sox2 protein in sphere-formed KMG4 on DN gel in Example 1(1).
Figure 7:
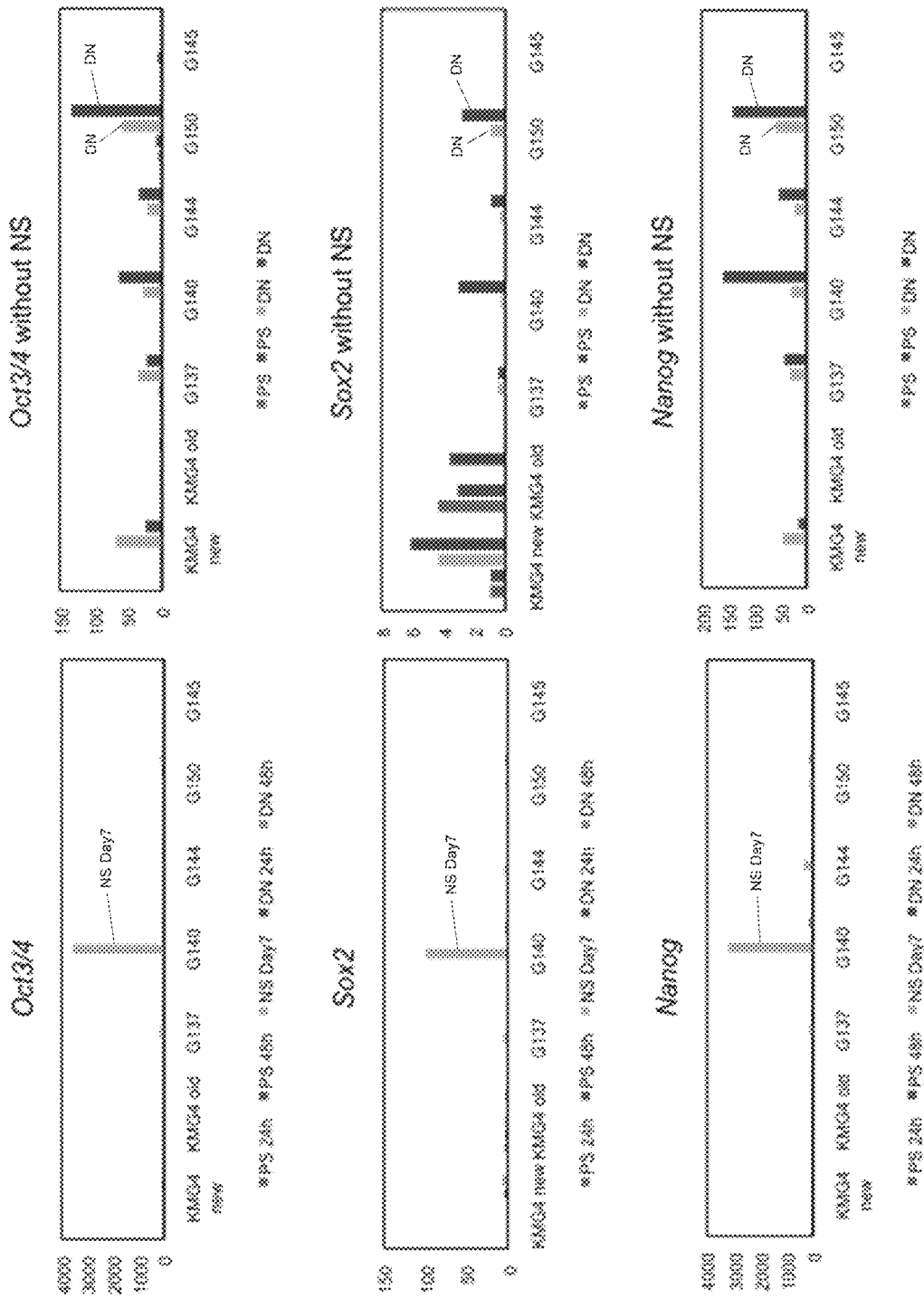
FIG. 7 indicates the results of confirming induction of expression of Sox2, Nanog and Oct3/4 mRNAs by qRT-PCR for brain tumor cell lines G137, G140, G144, G150 and G145 in Example 1(1).

After culturing KMG4, U138 and U343 for 3 days, induction of the expression of typical stem cell marker molecules (Sox2, Nanog, Oct3.4 mRNAs) was examined by qRT-PCR. Cells cultured in an ordinary polystyrene dish (PS dish) were used as a negative control. The results are shown in FIG. 5. Prominent induction of expression of the stem cell marker molecules on the DN gel was confirmed in comparison with cells cultured in the PS dish for each of the cells. In addition, induction of the expression of Sox2 protein was confirmed in sphere-formed KMG4 on the DN gel (FIG. 6). The results of confirming induction of expression of typical stem cell marker molecules (Sox2, Nanog, Oct3/4 mRNAs) by qRT-PCR for G137, G140, G144, G150 and G145 are shown in FIG. 7.

Figure 8A:
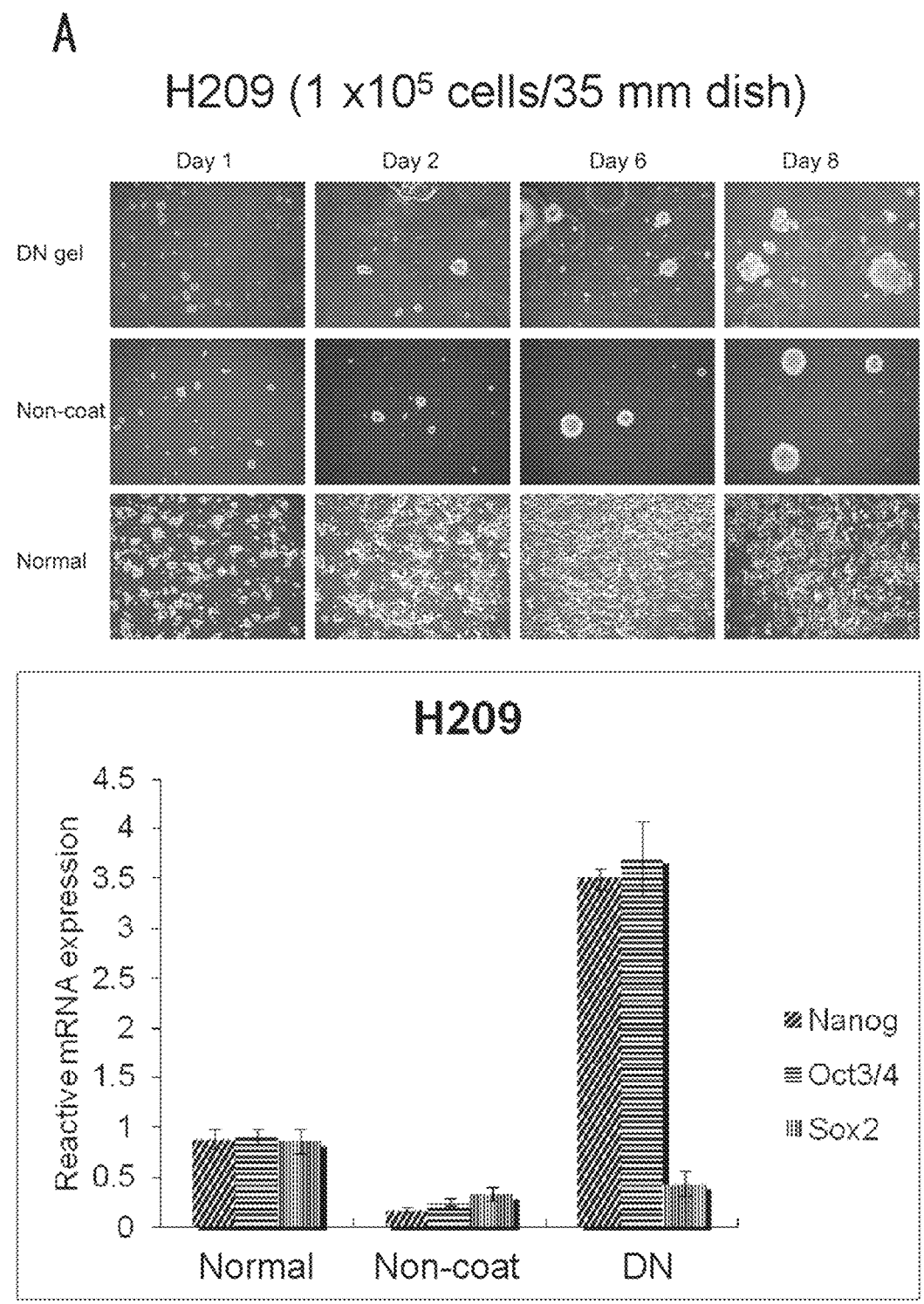
FIG. 8A indicates photographs of cells after culturing a lung cancer ell line (H209) and the results of confirming induction of expression of stem cell markers (Sox2, Nanog, Oct3/4 mRNAs) by qRT-PCR in Example 1(1).
Figure 9A:
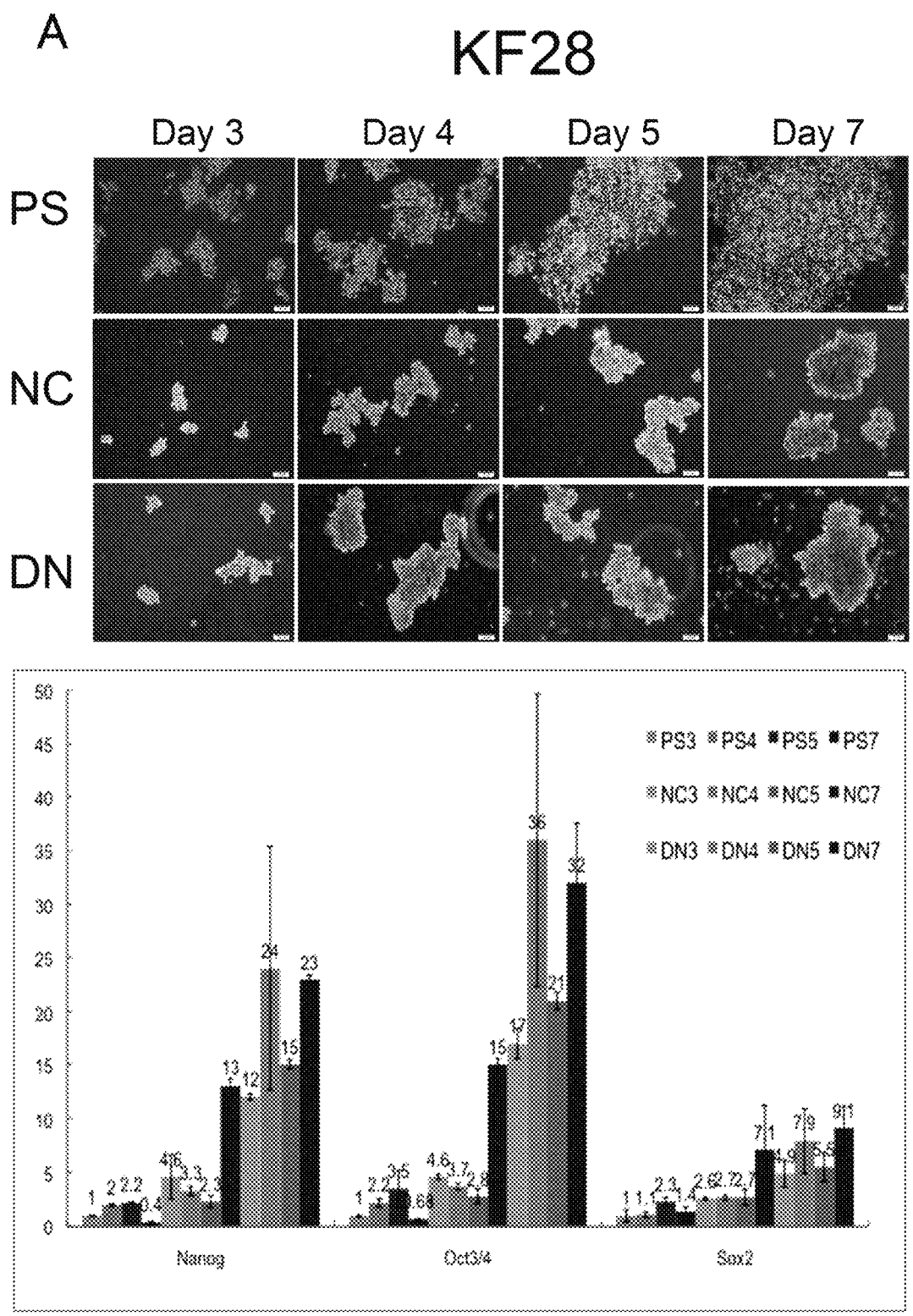
FIG. 9A indicates photographs of cells after culturing an ovarian cancer cell line (KF28) and the results of confirming induction of expression of stem cell markers (Sox2, Nanog, Oct314 mRNAs) by qRT-PCR (PS3 to PS7, NC3 to NC7 and DN3 to DN7 from left to right) in Example 1(1).
Figure 9B:
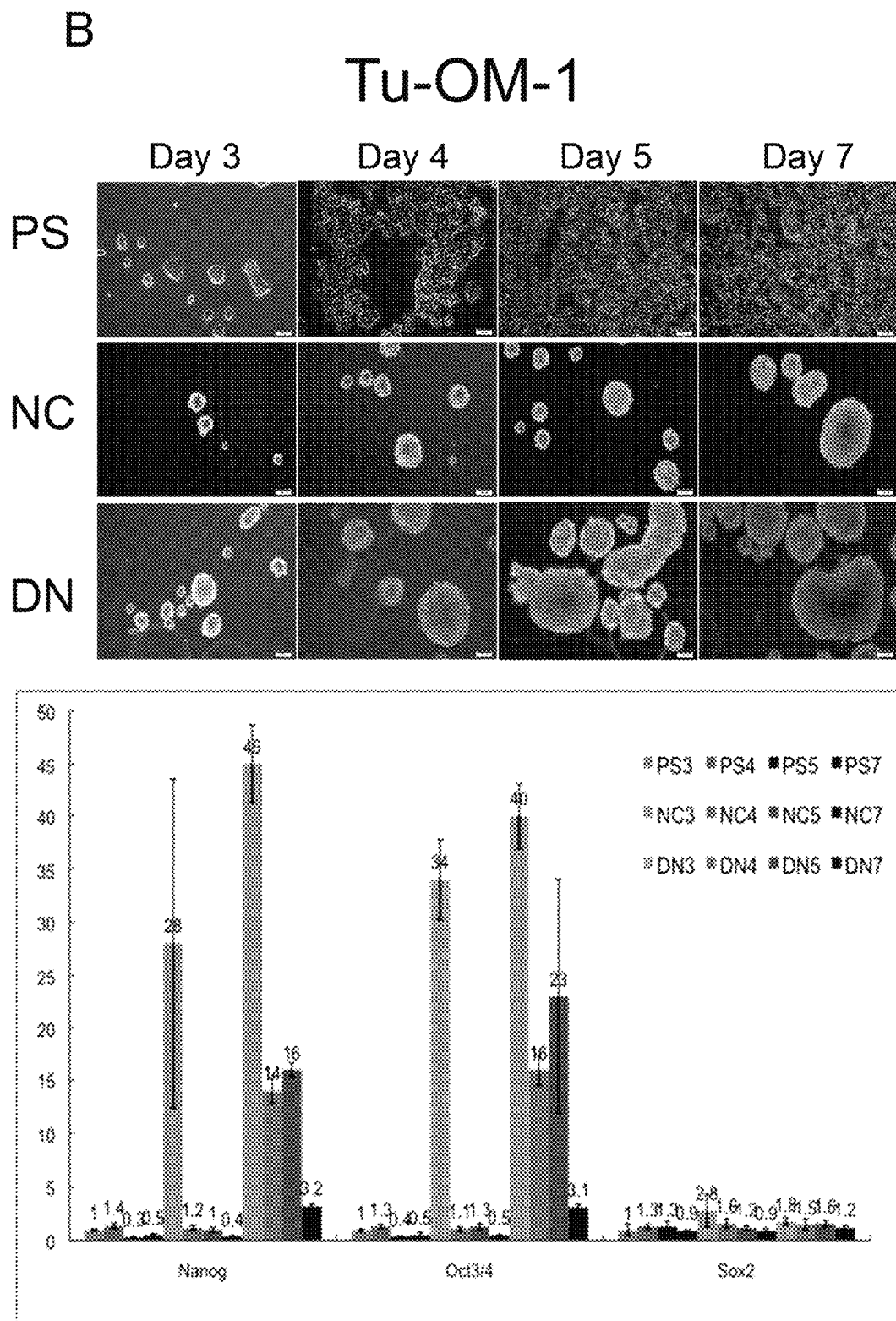
FIG. 9B indicates photographs of cells after culturing an ovarian cancer cell line (Tu-OM-1) and the results of confirming induction of expression of stem cell markers (Sox2, Nanog, Oct3/4 mRNAs) by qRT-PCR (PS3 to PS7, NC3 to N07 and DN3 to DN7 from left to right) in Example 1(1).

FIG. 8A and FIG. 8B indicate photographs of cells following culturing lung cancer cell lines (H209, SBC3) and the results of confirming induction of expression of stem cell marker molecules (Sox2, Nanog, Oct3/4 mRNAs) by qRT-PCR. FIG. 9A and FIG. 9B indicate photographs of cells following culturing of ovarian cancer cell lines (KF28, Tu-OM-1) and the results of confirming induction of expression of stem cell marker molecules (Sox2, Nanog, Oct3/4 mRNAs) by qRT-PCR.

Example 1(2)

Figure 10:
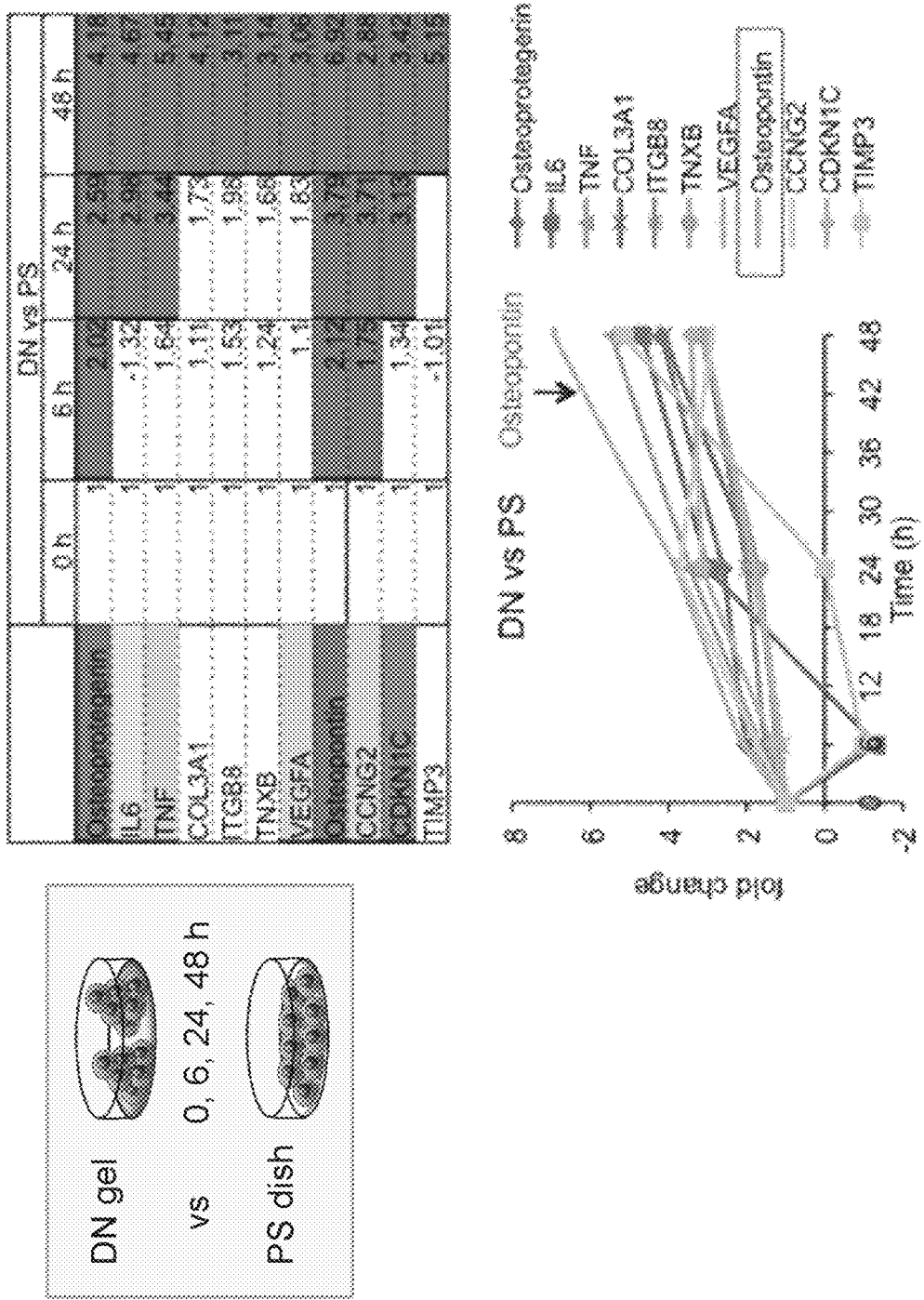
FIG. 10 indicates the results of microarray analyses (following extraction of total RNA from KMG4 cells cultured for 6, 24 and 48 hours and conversion to cDNA) in Example 1(2).
Figure 11:
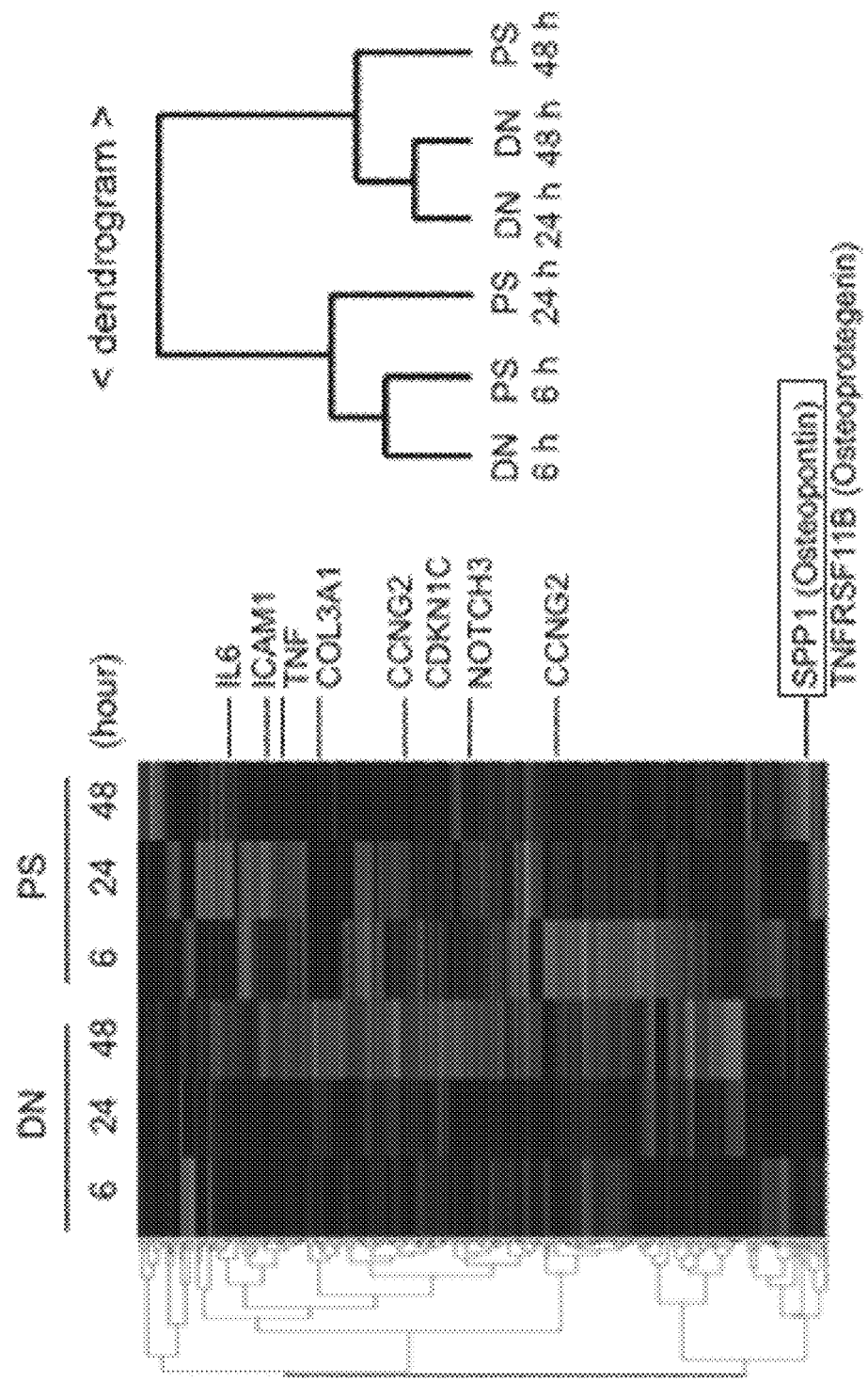
FIG. 11 indicates the results of microarray analyses (following extraction of total RNA from KMG4 cells cultured for 6, 24 and 48 hours and conversion to cDNA) in Example 1(2).

Elucidation of Mechanism Behind Induction of Expression of Brain Tumor Stem Cell Markers on Synthetic Polymer DN Gel A microarray analysis was carried out in order to elucidate the mechanism behind the induction of expression of stem cell markers in glioblastoma cell line KMG4 seeded on DN gel (SurePrint G3 Human GE 8×60K v2, Agilent Technologies). After extracting total RNA from KMG4 cells cultured on DN gel for 6, 24 and 48 hours and converting the total RNA to cDNA, the cDNA was subjected to microarray analysis. Cells cultured on a PS dish for 6, 24 and 48 hours were used as a negative control The results are shown in FIG. 10 and FIG. 11.

Eleven types of genes were identified for which expression increased by three-fold or more on DN gel in comparison with culturing on the PS dish at each of 6, 24 and 48 hours among the pathways for which expression fluctuated significantly on DN gel (osteoprotegerin, IL6, TNF, COL3A1, ITGB8, TNXB, VEGFA, osteopontin (SPP1), CDKN1C and TIMP3). Among them, those molecules for which increased expression was reconfirmed by qRT-PCR consisted of osteopontin and CDKN1C, and the gene that demonstrated the highest expression induction rate was osteopontin (SPP1). Expression of stem cell marker molecules decreased in cells in which osteopontin (SPP1) were knocked down by transfection with siRNA and cells treated with osteopontin neutralizing antibody in a confirmation experiment.

CD44 and ITG exist as osteopontin receptors, and the Hippo pathway has been determined to be activated from the osteopontin/CD44 signal pathway, while cell adhesion molecules including FAK and various types of kinase groups including Src, Akt, ERK and p38MAPK have been determined to be activated from the osteopontin/ITG pathway (see, for example, NPL 7). In the results of the present example as well, molecule activation patterns were determined to be broadly classified into three patterns when KMG4 cells are seeded on DN gel (see FIG. 12). These consist of (i) activation is increased in proportion of the cells depending on the time adhered on the DN gel (pFAK), (ii) activation begins soon after seeding on DN gel and remains activated (pAKT, p-p38MAPK), and (iii) activation consists of two peaks occurring at 6 hours and 48 hours after seeding the cells on DN gel (p-c-Met, pEGFR, pSrc, pERK). When Yap1, an important factor of the Hippo pathway, is knocked down by the siRNA method (knock-down efficiency: 80%), expression of each of Oct3/4, Sox2 and Nanog was determined to increase, while expression of stem cell marker molecules downstream from the Hippo pathway was determined to be suppressed in brain tumor cells.

Example 1(3)

Analysis of Tumor-Forming Ability of Cancer Stem Cells Induced on DN Gel in Vivo in Mice The following experiment was carried out in order to analyze the tumor-forming ability of cancer stem cells induced on DN gel in vivo in mice. The experiment method is as indicated below.
1. Stable gene introduction of tdTomato-Luc2 in KMG4 cells
2. Case of culturing tdTomato-Luc2-introduced KMG4 cells for 3 days on DN gel (group 1 below)
3. Transplantation of 500 cells into the brains of immunosuppressed mice (NOD/Shijic-scid Jcl)

Figure 13:
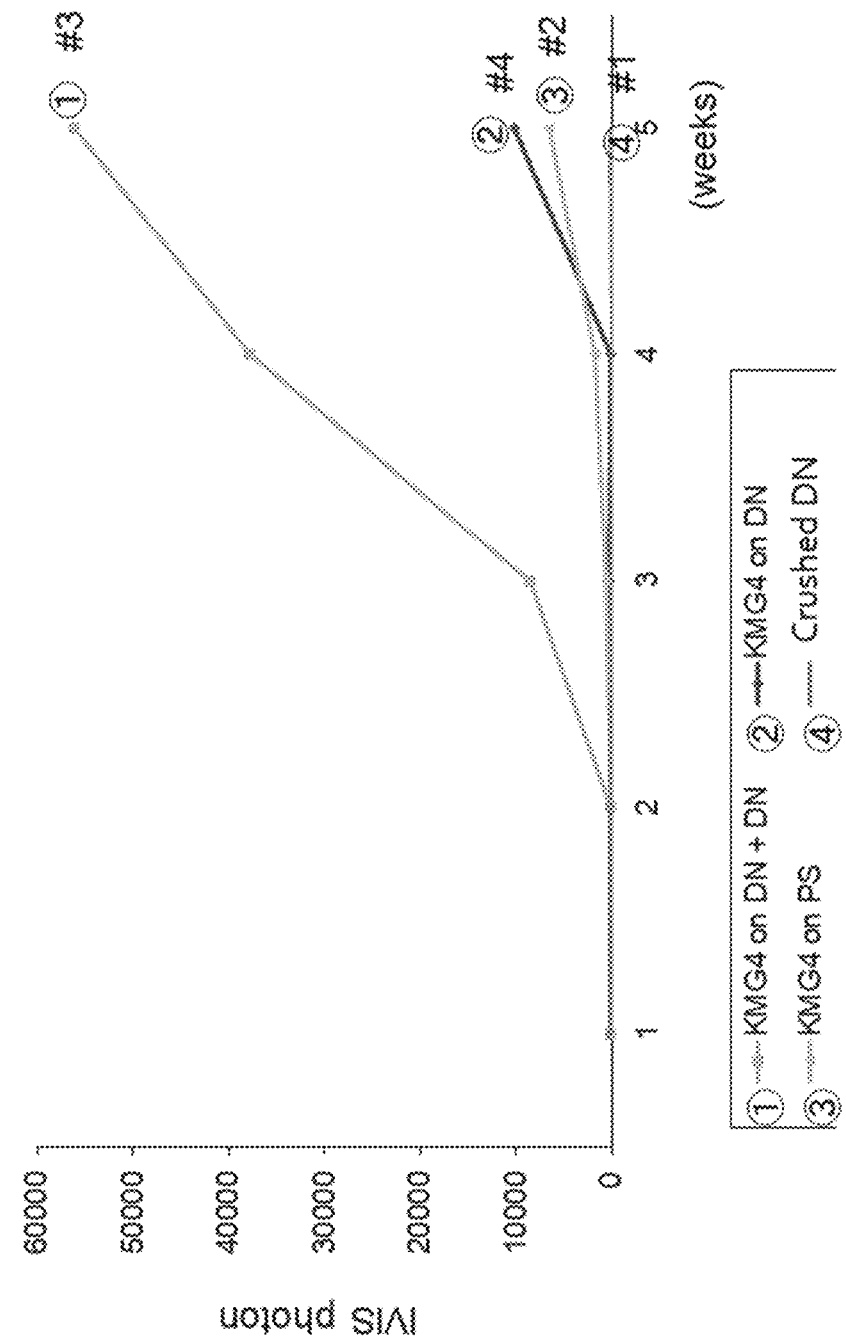
FIG. 13 indicates the results of analyzing tumor-forming ability in vivo in mice in Example 1(3).
Figure 14:
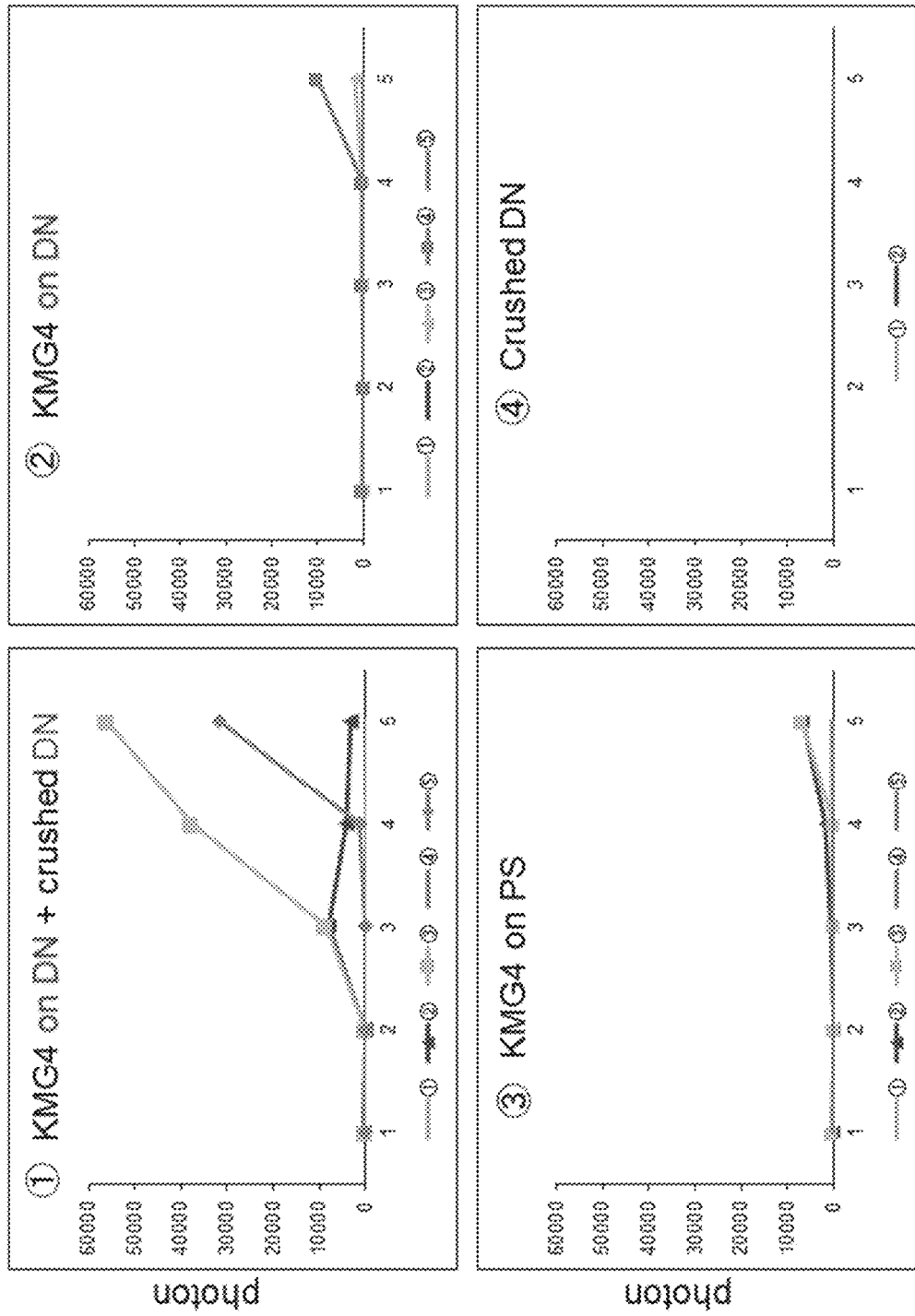
FIG. 14 indicates the results of analyzing tumor-forming ability in vivo in mice in Example 1(3).

The mice were divided into the following four groups: 1) mixed inoculation of KMG4 cells cultured for 3 days on DN gel with crushed DN gel (diameter: 100 μm or less); 2) inoculation of cells after culturing for days on DN gel; 3) inoculation of cells after culturing for 3 days on PS dish; and 4) inoculation of crushed DN gel only. 500 cells were inoculated in each group. The results are shown in FIG. 13 and FIG. 14. Prominent tumor formation was observed in the system consisting of mixed inoculation of gels seeded on DN gel with crushed DN gel of group 1). This suggests that continuous stimulation from DN gel is required to induce stemness.

Example 2(1)

Figure 15:
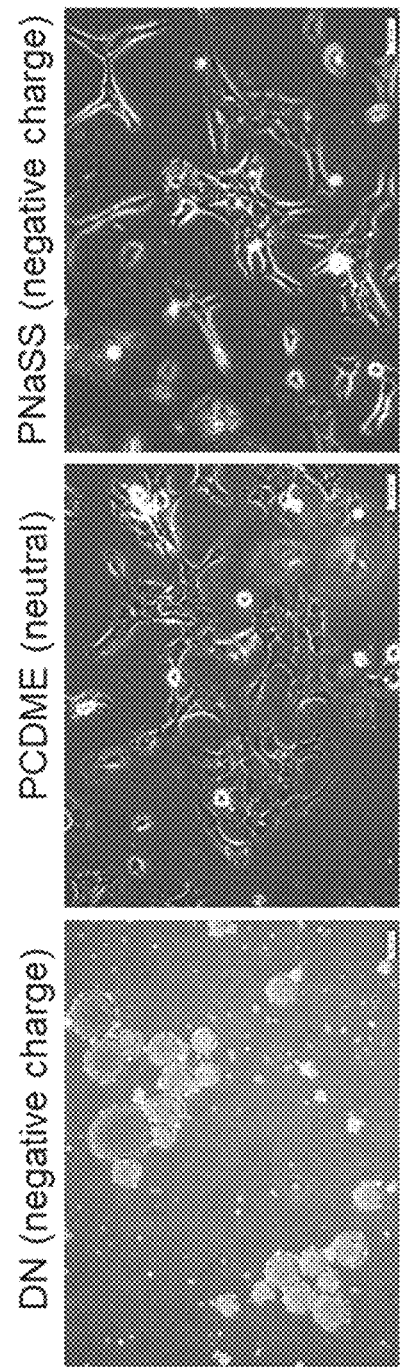
FIG. 15 indicates photographs of brain tumor cell line KMG4 cells on DN gel, PCDME gel and PNaSS gel in Example 2(1).
Figure 16:
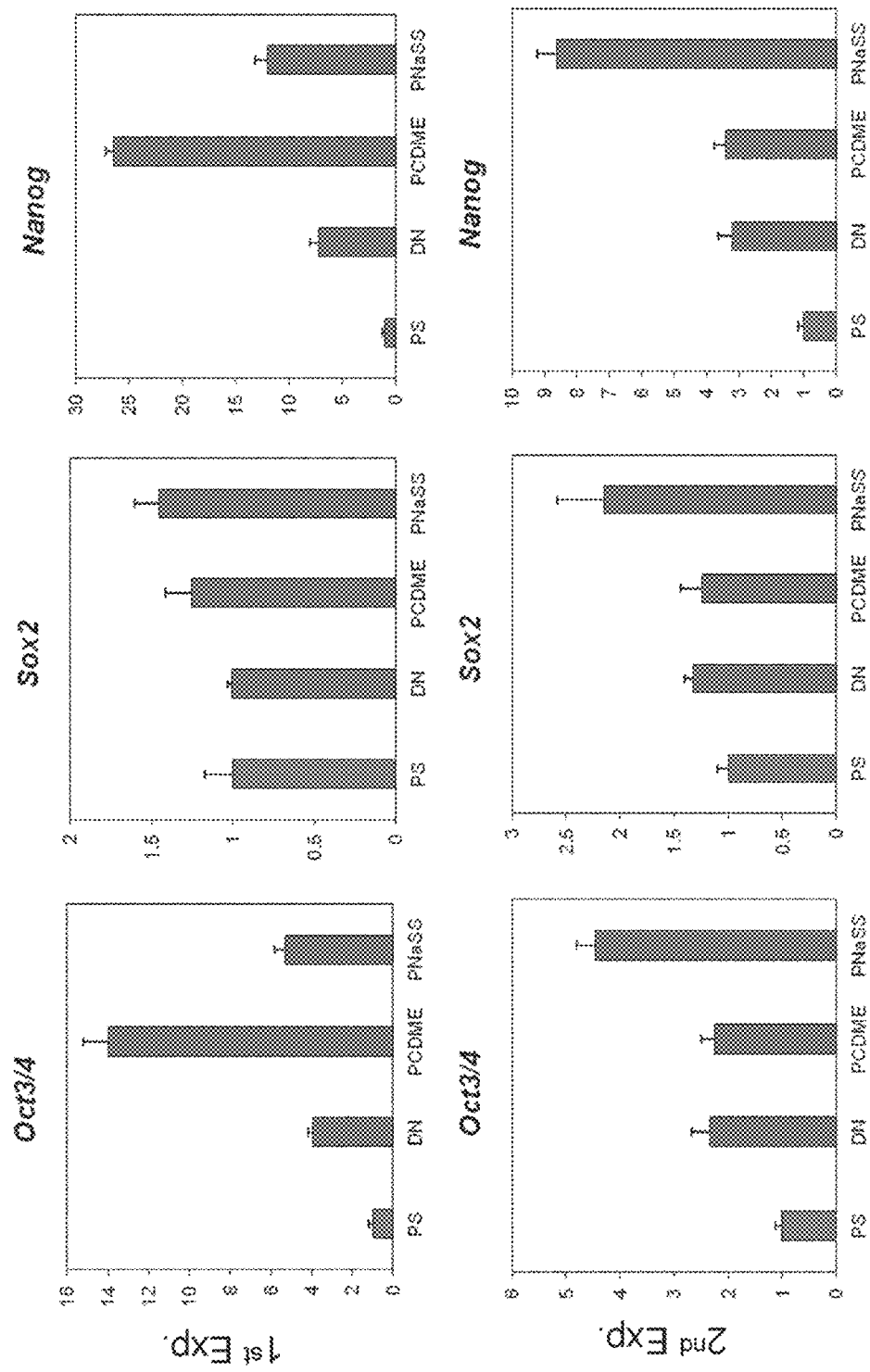
FIG. 16 indicates the results of confirming induction of expression of stem cell marker molecules (Sox2, Nanog, Oct3/4 mRNAs) by qRT-PCR in Example 2(1).
Figure 19:
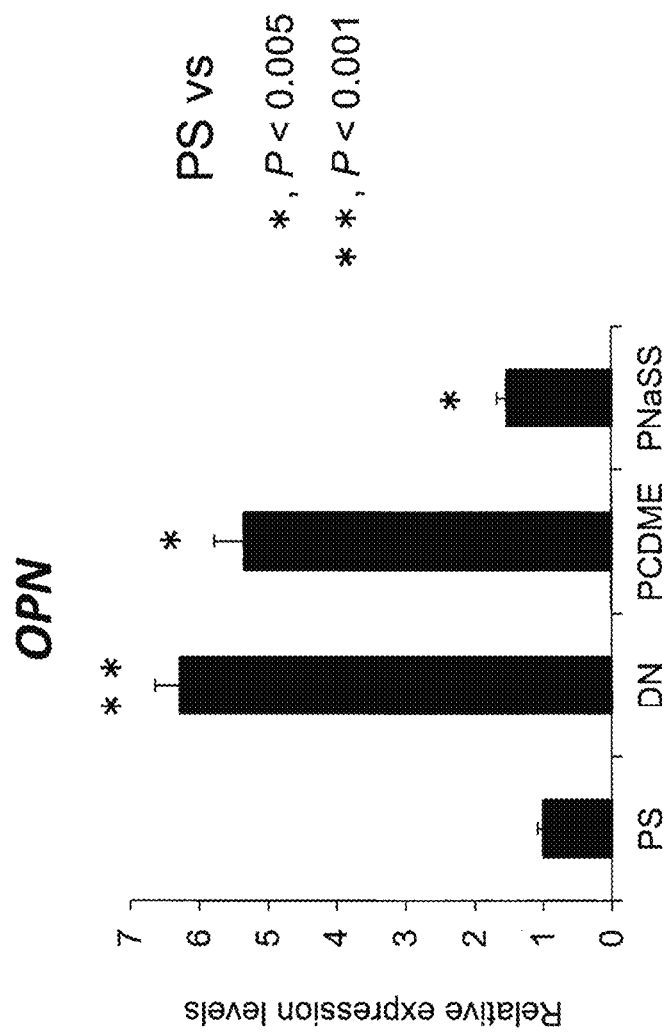
FIG. 19 indicates the results of confirming induction of expression of osteopontin (OPN) mRNA by qRT-PCR in Example 2(1).

Analysis of Induction of Expression of Brain Tumor Stem Cell Markers on Synthetic Polymer Gels Other than DN Gel Human brain tumor cell line (KMG4) cells were seeded at $1 \times 10^5$/mL on three types of synthetic polymer gels (DN, PCDME, PNaSS). FIG. 15 indicates photographs of cells cultured for 3 days. Moreover, the results of confirming induction of expression of stem cell marker molecules (Sox2, Nanog, Oct3/4 mRNAs) by qRT-PCR are shown in FIG. 16. In addition, the results of confirming induction of expression of osteopontin (OPN) mRNA by qRT-PCR are shown in FIG. 19. Cells cultured on an ordinary polystyrene culture dish (PS dish) were used as a negative control. Expression of stem cell marker molecules (Oct3/4, Sox2, Nanog mRNAs) and osteopontin (OPN mRNA) was confirmed to be induced in KMG4 cells cultured on PCDME and PNaSS gels. As shown in FIG. 15, cells seeded on DN gel formed spheres and the cells adhered to and extended from the PCDME and PNaSS gels Example 2(2)

Figure 17:
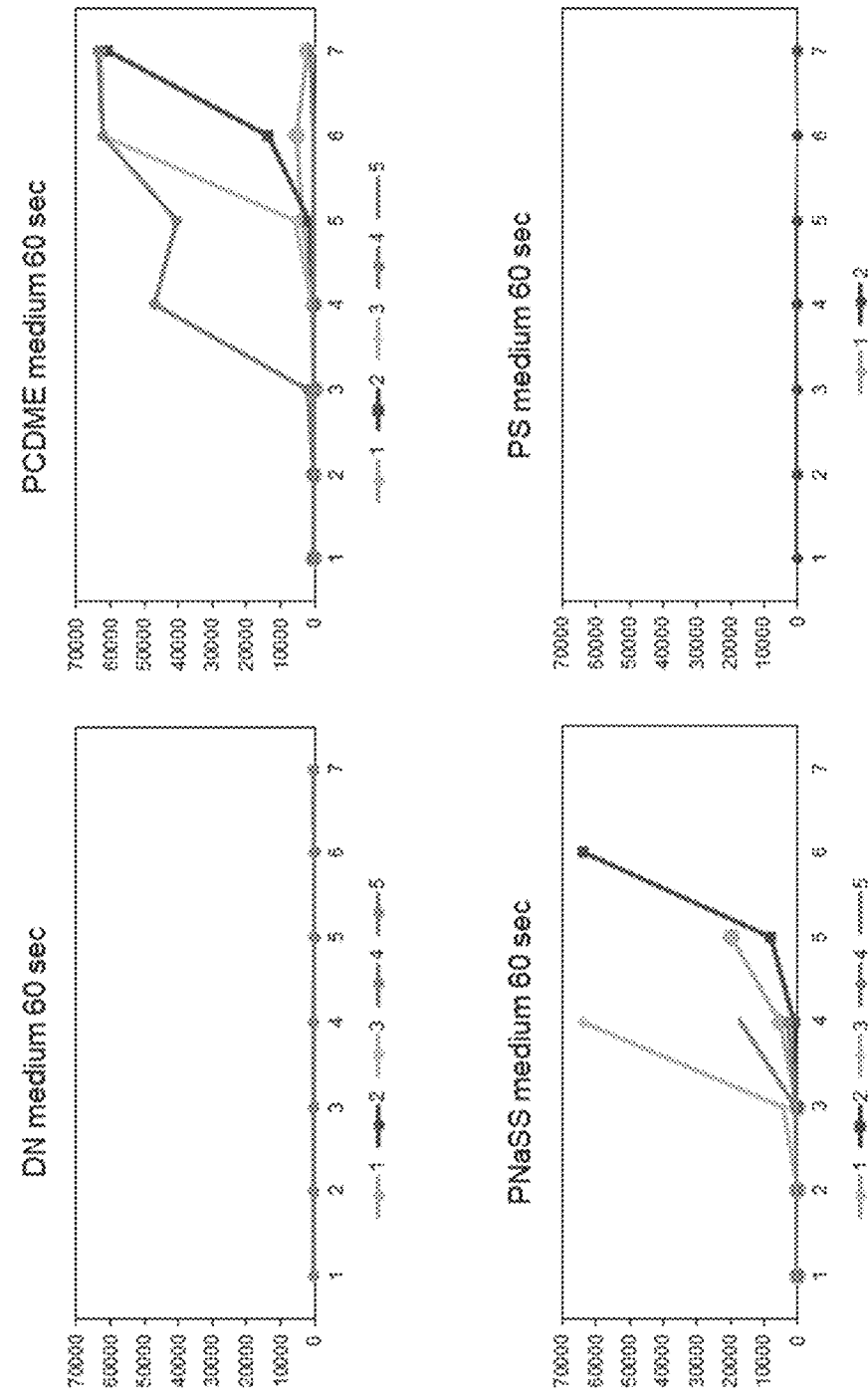
FIG. 17 indicates the results of analyzing tumor-forming ability in vivo in mice by synthetic polymer gel-induced brain tumor stem cells in Example 2(2).

Analysis of Tumor-Forming Ability of Synthetic Polymer Gel-Induced Brain Tumor Stem Cells in Vivo in Mice An analysis was carried out as to whether or not cancer stem cells induced or PCDME and PNaSS gels have the ability to foam tumors in vivo in mice (FIG. 17). 500 KMG4-luc cells cultured for 3 days on PCDME and PNaSS gels were inoculated into the brains of NOD/ShinJic-scid mice followed by observing tumor formation and growth over time using an IVIS system. Tumor formation was observed at three weeks after injection in all mice injected KMG4 cells cultured on PNaSS gel, and all of the mice died of cancer at seven weeks after inoculation. KMG4 cells inoculated on PCDME gel formed prominent tumors roughly one week later than in the case of PNaSS gel. Tumor-forming ability induced by both gels increased more prominently than that induced by DN gel. On the basis of these results, although continuous stimulation from DN gel was required for DN gel to induce cancer stem cells (group 3 above), PNaSS and PCDME gels were suggested to have the potential to be able to irreversibly induce conversion of cancer cells to cancer stem cells both alone and in a short period of time.

Example 3

Figure 18:
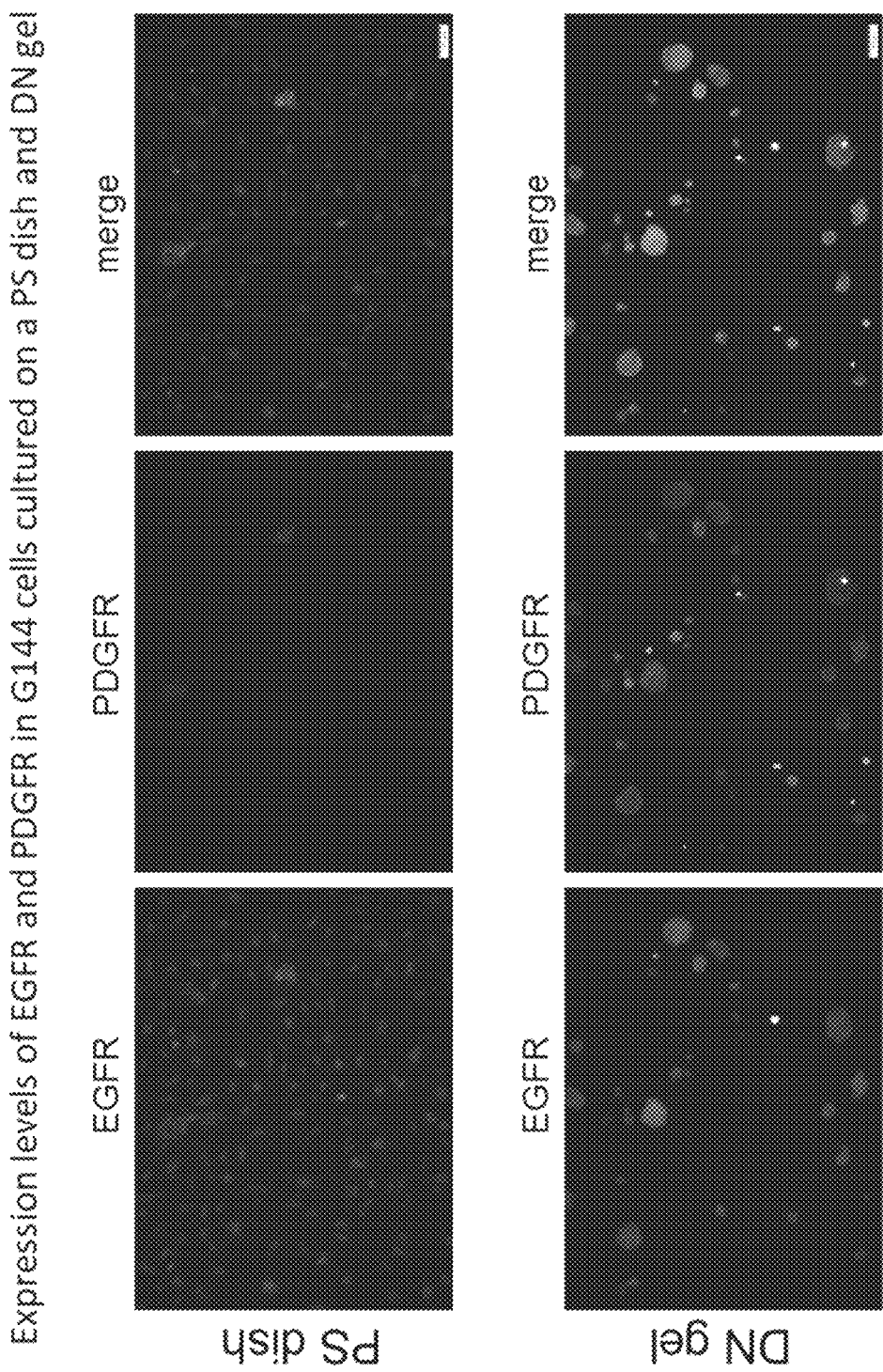
FIG. 18 indicates the results of testing conversion of cancer patient-derived primary cultured cells to stem cells by polymer gel in Example 3. The photographs indicate the expression levels of EGFR and PDGFR in G144 cells cultured on a PS dish and DN gel.

Conversion of Primary Cultured Cells Derived from Cancer Patients to Stem Cells by Polymer Gel A study was conducted as to whether or not polymer gel induces conversion of cells derived from actual patients to cancer stem cells and suggests a therapeutic target. Although G144 cells derived from patients with malignant brain tumors express EGF receptors under ordinary culture conditions, expression of PDGF receptors is observed only to the degree of being expressed in several cells. Induction of expression of PDGF receptors was observed in G144 cells in which sphere formation was induced by polymer gel (FIG. 18). The growth of stem cells induced by polymer gel was suppressed by anti-PDGFR antibody in a treatment study. The above results suggest that polymer gel makes it possible to diagnosis stem cell profiles following relapse for samples obtained from cancer patients prior to treatment.

Example 4

Figure 20:
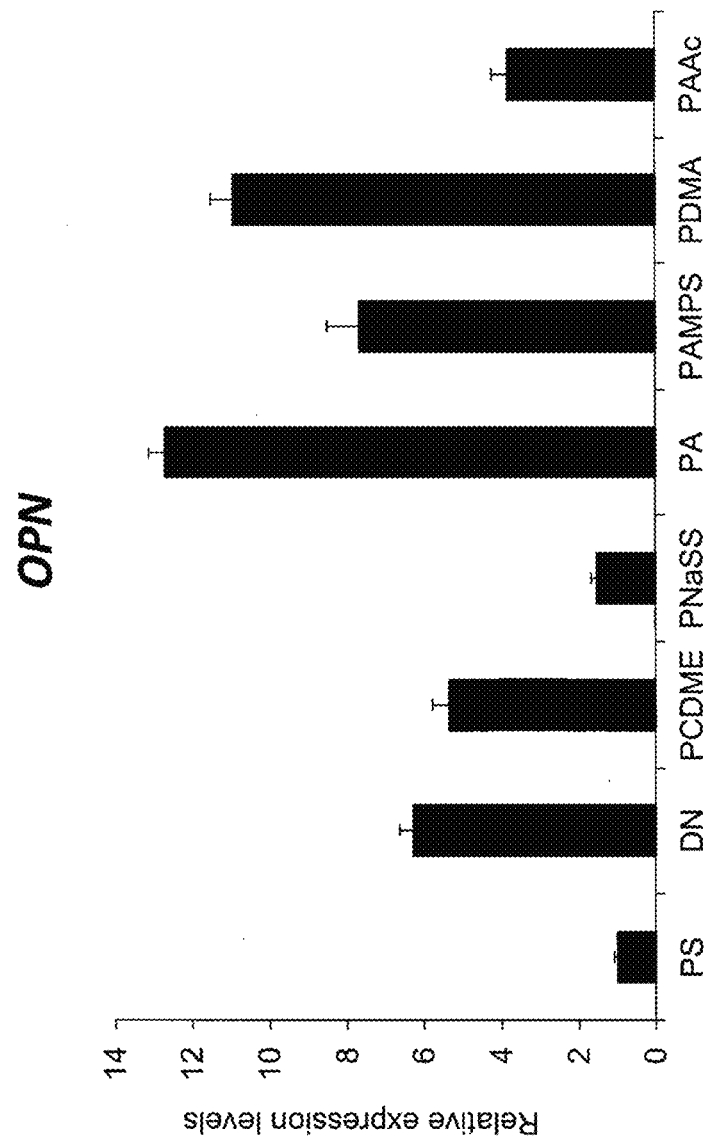
FIG. 20 indicates the results of confirming induction of expression of osteopontin (OPN) mRNA in KMG4 cells cultured on four types of polymer gels (PA, PAMPS, PDMA and PAAc gel) by qRT-PCR along with the results in cells cultured in DN, PCDME and PNaSS gels in Example 4.
Figure 22:
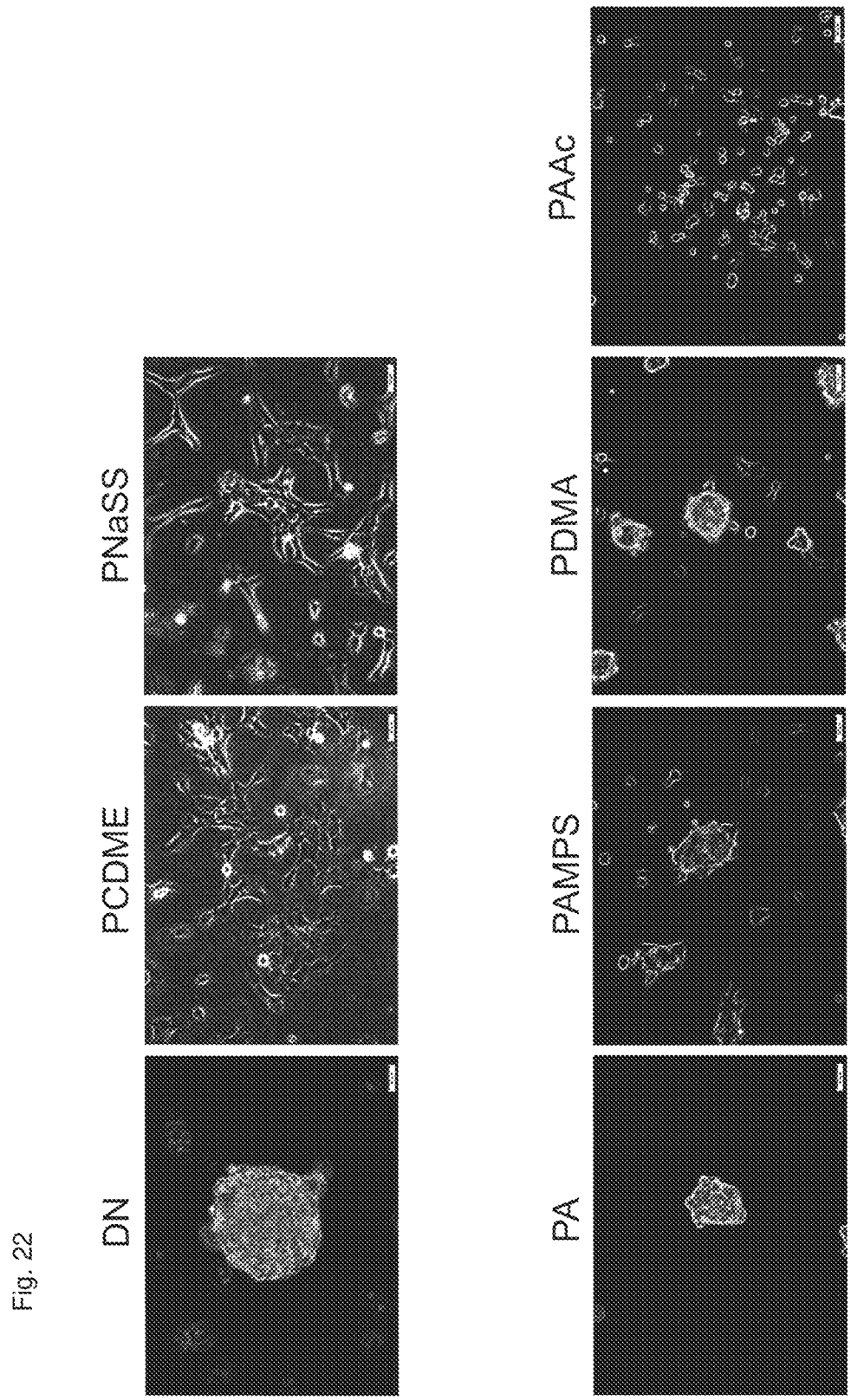
FIG. 22 indicates photographs of brain tumor KM G4 cells on four types of polymer gels (PA, PAMPS, PDMA and PAAc gels) along with photographs of the cells cultured on DN, PCDME and PNaSS gels in Example 4.

Culturing on Four Types of Synthetic Polymer Gels Consisting of PA, PAMPS, PDMA and PAAc Analyses were further carried out using four types of synthetic polymer gels (PA, PAMPS, PDMA, PAAc). Human brain tumor cell line (KMG4) cells were seeded at $1 \times 10^5$ cells/mL on synthetic polymer gels consisting of PA, PAMPS, PDMA and PAAc and cultured for 3 days, and the results of confirming induction of expression of osteopontin (OPN) mRNA by qRT-PCR are shown in FIG. 20, while the results of confirming stem cell marker molecules (Oct3/4 and Nanog mRNAs) by qRT-PCR are shown in FIG. 21. Cells cultured on an ordinary polystyrene dish (PS dish) were used as a negative control. FIG. 20 and FIG. 21 also indicate the expression analysis results for each of DN, PCDME and PNaSS gels for comparison. Induction of expression of stem cell marker molecules (Oct3/4 and Nanog mRNAs) and osteopontin (OPN) mRNA was confirmed in KMG4 cells cultured on PA, PAMPS, PDMA and PAAc gels in addition to that on DN, PCDME and PNaSS gels. As shown in FIG. 22, KMG4 cells seeded on PA, PAMPS and PDMA gels and then cultured for 3 days formed spheres. Although KMG4 cells seeded and cultured in the same manner on PAAc gel adhered loosely to the gel, extension on the gel was not observed (adhesive, non-extending), FIG. 22 also indicates photographs of KMG4 cells seeded on DN, PCDME, and PNaSS gels and cultured for 3 days (DN: sphere formation, PCDME and PNaSS: adhesion and extension).

INDUSTRIAL APPLICABILITY

The present invention is useful in tumor-related fields in which stem cells are involved.

We claim:

1. A method of producing cancer stem cells from brain, lung or ovarian cancer tissue, comprising:
    culturing a living cell population from said cancer tissue in the presence of a gel substance to obtain a living cell population containing brain, lung or ovarian cancer stem cells,
    wherein said gel substance is a synthetic polymer gel that induces expression of osteopontin in cells present in the living cell population obtained from cancer tissue, and converts at least a portion of said cells contained in the living cell population in to cancer stem cells; and
    said synthetic polymer gel is composed of poly(sodium p-styrene sulfonate) (PNaSS) gel, poly-N-(carboxymethyl-N,N-dimethyl-2-(methacryloyloxy) ethanaminium (PCDME) gel, polyampholyte (PA) gel, poly(2-acrylamido-2-methyl-1-propanesulfonic acid) (PAMPS) gel, poly(N,N'-dimethylacrylamide) (PDMA) gel, poly(acrylic acid) (PAAc) gel, or double network gel having an interpenetrating network structure of PAMPS gel and PDMA gel.

2. The method according to claim 1, wherein the living cell population containing cancer stem cells contains cells exhibiting a spherical structure.

3. The method according to claim 1, wherein cells in the living cell population containing cancer stem cells have a higher expression level of Oct3/4, Sox2 and/or Nanog than that prior to culturing in the presence of the gel substance.

4. The method according to claim 1, wherein the quality and/or quantity of cancer stem cells in the living cell population is measured.

5. The method according to claim 1, further comprising transplanting the cancer stem cell into mice.

6. The method of claim 1, wherein the double network gel is in the form of a sheet or particles.

7. The method according to claim 4, comprising
    a) contacting said the living cell population comprising cancer stem cells with an test substance; and
    b) determining the effects of said test substance on cancer stem cells in the population.

8. The method according to claim 1, wherein the culturing is carried out in vitro.

* * * * *